(12) United States Patent
Nagase et al.

(10) Patent No.: US 8,632,563 B2
(45) Date of Patent: Jan. 21, 2014

(54) SURGICAL INSTRUMENT

(75) Inventors: Toru Nagase, Tachikawa (JP); Kazunori Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1939 days.

(21) Appl. No.: 10/841,909

(22) Filed: May 7, 2004

(65) Prior Publication Data

US 2004/0225323 A1 Nov. 11, 2004

(30) Foreign Application Priority Data

May 8, 2003 (JP) ................................. 2003-130726

(51) Int. Cl.
*A61B 17/00* (2006.01)

(52) U.S. Cl.
USPC ............................ 606/205; 606/206; 606/207

(58) Field of Classification Search
USPC .......... 606/205–210, 139, 142, 143, 144, 151
See application file for complete search history.

(56) References Cited

U.S. PATENT DOCUMENTS

| 4,950,273 | A |   | 8/1990  | Briggs                   |
|-----------|---|---|---------|--------------------------|
| 5,330,502 | A | * | 7/1994  | Hassler et al. ... 606/205|
| 5,350,391 | A |   | 9/1994  | Iacovelli                |
| 5,374,277 | A |   | 12/1994 | Hassler                  |
| 5,549,637 | A |   | 8/1996  | Crainich                 |
| 5,607,450 | A | * | 3/1997  | Zvenyatsky et al. ... 606/206 |
| 5,609,601 | A | * | 3/1997  | Kolesa et al. ... 606/170 |
| 5,643,294 | A | * | 7/1997  | Tovey et al. ... 606/148  |
| 5,649,957 | A | * | 7/1997  | Levin ... 606/207         |
| 5,797,959 | A | * | 8/1998  | Castro et al. ... 606/207 |
| 5,836,960 | A | * | 11/1998 | Kolesa et al. ... 606/170 |
| 7,476,237 | B2| * | 1/2009  | Taniguchi et al. ... 606/205 |

FOREIGN PATENT DOCUMENTS

| JP | 07-255735   | 10/1995 |
| JP | 08-164141   | 6/1996  |
| JP | 08-206120   | 8/1996  |
| JP | 2003-010196 | 1/2003  |

* cited by examiner

*Primary Examiner* — Darwin Erezo
(74) *Attorney, Agent, or Firm* — Scully, Scott, Murphy & Presser, P.C.

(57) ABSTRACT

A surgical instrument having including a fixed handle and a pivoting handle, an elongated treatment part operating rod connected to the pivoting handle which advances and retracts with the operation of the pivoting handle, an insertion part through which the operating rod is inserted, a pivoting base supported on the distal end portion of the insertion part via a pivoting shaft so that the pivoting base is free to pivot, an elongated pivoting base operating rod whose distal end portion is connected to the pivoting base which causes the pivoting base to pivot about the pivoting shaft, a treatment part base which is connected to the pivoting base, and on which a surgical treatment part which performs an opening-and-closing action is disposed, and a joint member having a plurality of universal joints connects the treatment part operating rod and the surgical treatment part disposed on the treatment part base.

7 Claims, 29 Drawing Sheets

SURGICAL INSTRUMENT

This application claims benefit of Japanese Application No. 2003-130726 filed on May 8, 2003, the contents of which are incorporated by this reference.

BACKGROUND OF THE INVENTION

1. Field of the Invention

The present invention relates to a surgical instrument which is used when a surgical procedure, especially a surgical procedure that is performed under an endoscope, is performed by actuating a surgical treatment part disposed on the distal end portion of the insertion part of this instrument in a state in which an operating part disposed on the proximal end portion of this insertion part is gripped by the operator performing the surgical procedure.

2. Description of the Related Art

In the past, endoscopes which make it possible to perform various types of treatments on treatment sites while observing an object image with the endoscope (which has an insertion part formed as an elongated part) inserted into body cavities or the like have been widely used.

In recent years, furthermore, surgical procedures or the like in which therapeutic measures or treatments are performed under endoscopic observation without opening the abdomen have been performed in order to reduce the degree of invasion of a patient's body. In such surgical procedures, an endoscope used for observation is guided into a body cavity via a trocar, and a surgical instrument is guided to the treatment side inside the body cavity through this trocar. Then, a therapeutic procedure or treatment is performed while observing the surgical instrument and treatment site by means of the endoscope.

The surgical instrument that is used in surgical procedures or the like performed under an endoscope is long and slender, and is devised so that a surgical treatment part (hereafter also referred to as a "treatment member") disposed on the distal end portion of the insertion part is actuated by operating an operating part disposed on the proximal end of the insertion part.

For example, instruments in which a treatment member disposed on the distal end is devised such that this treatment member can freely pivot with respect to the main axis of the surgical instrument and such that the treatment member that has thus been pivoted can be rotated about its own axis or the like are described in U.S. Pat. No. 5,374,277, U.S. Pat. No. 5,549,637 and U.S. Pat. No. 5,350,391.

In concrete terms, in the surgical instrument described in U.S. Pat. No. 5,374,277, the instrument comprises a pivoting joint that allows pivoting of the distal end portion with respect to the main axis of the surgical instrument, and comprises a mount for the treatment member on the distal end side of this pivoting joint. This mount has a construction which is divided by wrist means into a first mount on the distal end side and a second mount on the proximal end side. As a result, the treatment member disposed on the distal end portion of the first mount can be rotated about the axis on the distal end side of the pivoting joint.

The medical instrument described in U.S. Pat. No. 5,549,637 has a joint part. In this medical instrument, the distal end portion can pivot with respect to the main axis of the medical instrument, and can also rotate about the axis on the distal end side of the pivoting joint. Flexible driving means such as a wire, cable or the like are disposed in the pivoting mechanism of the distal end portion. Furthermore, spur gears or bevel gears are used in the respective parts of the operating part, pivoting joint part and the like as mechanisms for causing the rotation of the part on the distal end side of the pivoting joint about the axis. Moreover, a push rod form member is installed via a link part in the mechanism that operates the treatment member mounted on the distal end.

In the laparoscopic instrument described in U.S. Pat. No. 5,350,391, the pivoting operation of a treatment member installed on the distal end is performed by one handle of a pair of operating handles, and the operation of the opening-and-closing movement of this treatment member is performed by the other handle of this pair of operating handles.

SUMMARY OF THE INVENTION

The surgical instrument of the present invention is constructed from a treatment part opening-and-closing operating part which also serves as a gripping part, and which comprises a fixed handle and a pivoting handle, an elongated treatment part operating rod having rigidity which is connected to the pivoting handle of this treatment part opening-and-closing operating part, and which advances or retracts in accordance with the operation of the pivoting handle, an insertion part through which the treatment part operating rod is inserted, a pivoting base which is pivotably shaft-supported on the distal end portion of the insertion part via a pivoting rod that is disposed perpendicular to the longitudinal axis of the insertion part, an elongated pivoting base operating rod having rigidity whose distal end portion is connected to the pivoting base, and which causes the pivoting base to pivot about the pivoting shaft by advancing and retracting, a treatment part base which is connected to the pivoting base, and on which a surgical treatment part that performs an opening-and-closing action in accordance with the advancing and retracting action of the treatment part operating rod is disposed, and a joint member having a plurality of universal joints which forms a connecting part having rigidity that connects the treatment part operating rod and the surgical treatment part disposed on this treatment part base. Accordingly, the pivoting base is caused to pivot about the pivoting shaft by causing the pivoting base operating rod to advance or retract, and the surgical treatment part is caused to pivot in linkage with this. Furthermore, the surgical treatment part is opened or closed into a desired state or caused to rotate into a desired position by further causing the treatment part operating rod to advance or retract or rotate about the axis in a desired state of pivoting. Furthermore, since the treatment part operating rod and base operating rod are constructed from members that possess rigidity, and since this treatment part operating rod and surgical treatment part are connected by a connecting part that possesses rigidity, the handling operation at the proximal end is reliably transmitted so that the desired operation can be reliably performed.

The above and other objects, features and advantages of the invention will become more clearly understood from the following description referring to the accompanying drawings.

DESCRIPTION OF THE PREFERRED EMBODIMENTS

Embodiments of the present invention will be described below with reference to the attached drawings.

FIGS. 1 through 27 illustrate a first embodiment of the present invention. FIGS. 1 through 10 are diagrams that illustrate the construction of the surgical instrument. Meanwhile, FIGS. 11 through 27 are diagrams used to illustrate the operation of the surgical instrument.

Figure 1:
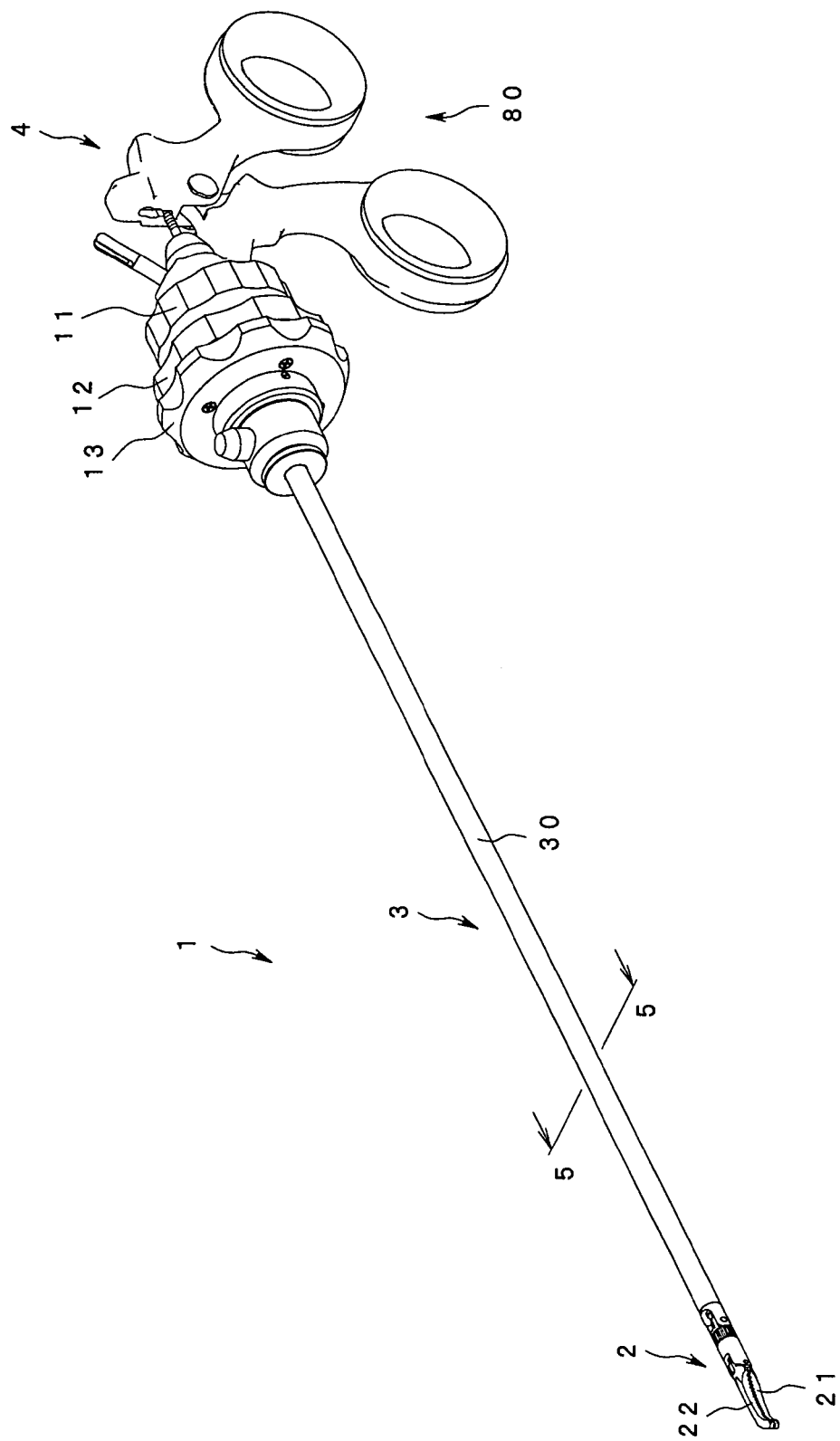
FIG. 1 is a diagram which illustrates the surgical instrument.

As is shown in FIG. 1, the surgical instrument 1 of the present embodiment is constructed mainly from a surgical treatment part (hereafter abbreviated to "treatment part") 2, an insertion part 3, and a gripping operating part 4 which also serves as a gripping part.

For example, the treatment part 2 constitutes dissection forceps, and is constructed so that a first treatment piece 21 and second treatment piece 22 comprising a pair of treatment parts that possess rigidity can be freely opened and closed. The insertion part 3 has an elongated insertion tube 30. The gripping operating part 4 comprises a treatment part opening-and-closing operating part 80 that opens and closes the first operating part 21 and second operating part 22 constituting the operating part 2.

A first knob 11, second knob 12 and third knob 13 that constitute substantially circular pivoting operating parts (described later) are disposed in the vicinity of the gripping operating part 4 at the proximal end of the insertion part 3 in the numbered order from this gripping operating part 4. As a result, the instrument is devised so that an operator can operate the respective knobs 11, 12 and 13 with the middle finger and index finger while holding the fixed handle 81 and pivoting handle 82 with the thumb and ring finger. In other words, the instrument has a construction which is such that all of the operations of the surgical instrument 1 can be performed by the operator with one hand.

Figure 2:
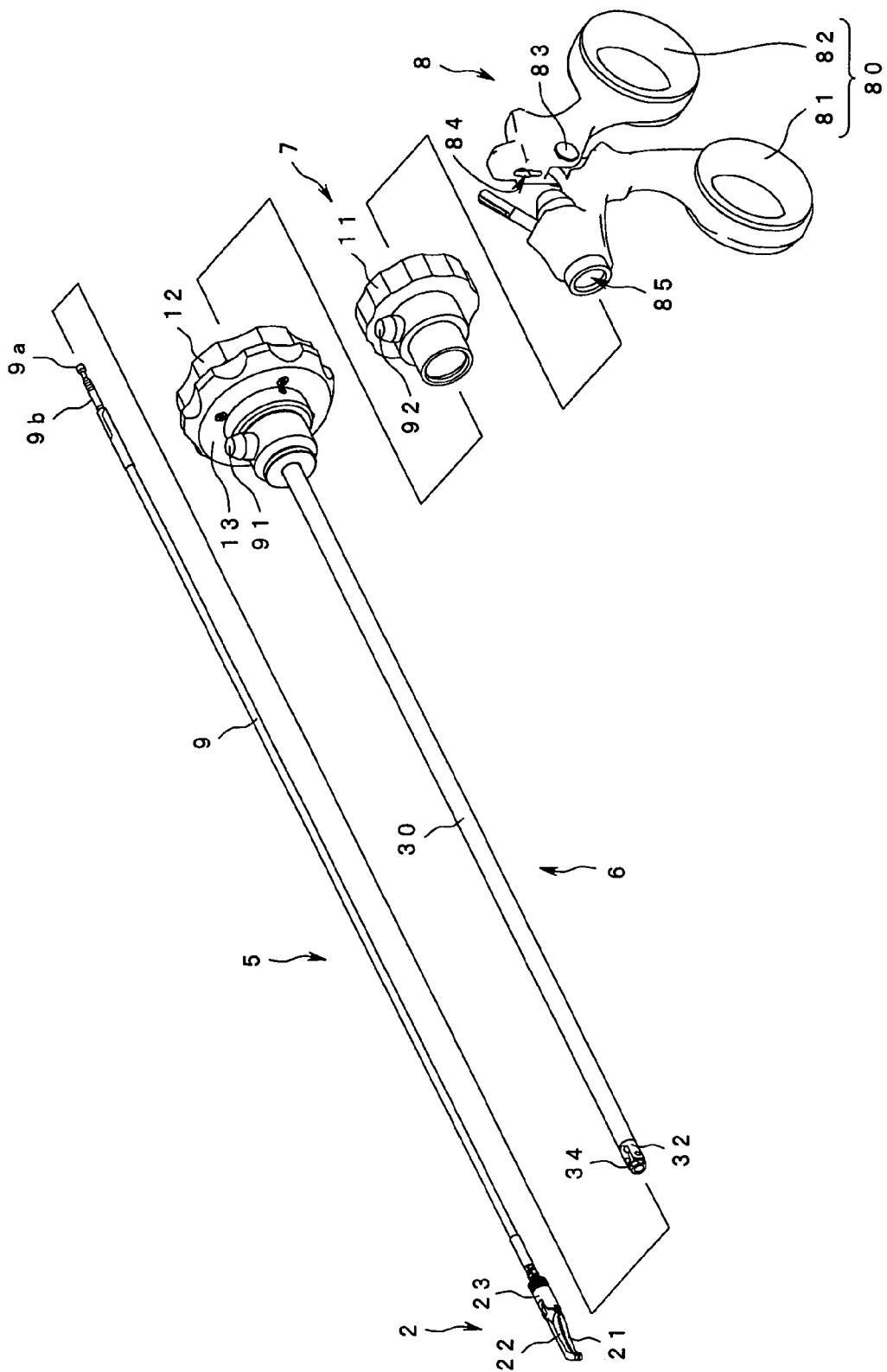
FIG. 2 is a diagram which shows the surgical instrument in an exploded state.

As is shown in FIG. 2, the surgical instrument 1 has a construction which is separated into a treatment part unit 5, an insertion tube unit 6, a treatment part rotating unit 7 and a gripping operating unit 8 in a manner that allows free attachment and detachment.

The treatment part unit 5 comprises the treatment part 2 and the like. The insertion tube unit 6 comprises the second knob 12, the third knob 13, the insertion tube 30 and the like. The treatment part rotating unit 7 comprises the first knob 11. The gripping operating unit 8 constitutes the treatment part opening-and-closing operating part.

Figure 3:
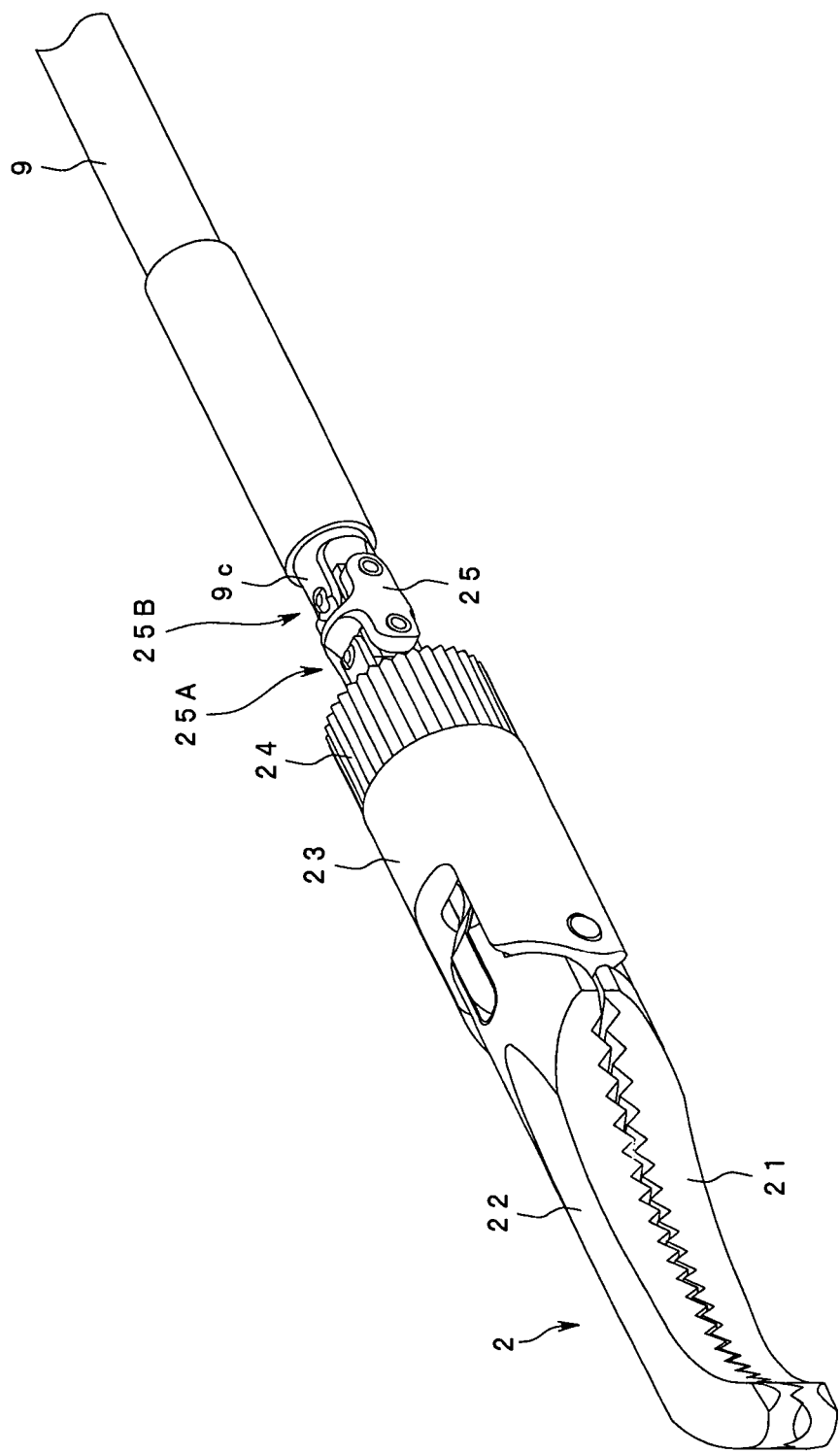
FIG. 3 is a diagram which illustrates the construction of the distal end portion of the treatment part unit.

As is shown in FIGS. 2 and 3, the treatment part unit 5 is constructed mainly from a tubular treatment part base 23, a treatment part unit attachment and detachment member (hereafter abbreviated to "unit attachment and detachment member") 24, and a treatment part operating rod 9.

The treatment part base 23 is connected to the treatment parts 21 and 22, i.e., to the proximal end parts of these treatment parts 21 and 22. The unit attachment and detachment member 24 is an annular member which is disposed with free play on the proximal end portion of the treatment part base 23.

A female screw part 24a shown in FIG. 7 (described later) is formed in the inner circumferential surface of the unit attachment and detachment member 24. The treatment part operating rod 9 opens and closes the treatment part 2. The treatment part operating rod 9 is formed with a specified length dimension from a rigid member.

A rotational driving rod 9b which has a ball part 9a is integrally disposed on the proximal end portion of the treatment part operating rod 9. Planar parts 9c and 9d shown in FIG. 10 (described later) are formed in specified positions on the side surface parts of the rotational driving rod 9b.

Furthermore, in this construction, the treatment part operating rod 9 and the treatment part 2 are connected via a connecting member 28 constituting the connecting part shown in FIG. 7 (described later), a joint member 25 with a specified shape comprising two sets of universal joints 25A and 25B and the like.

Figure 8:
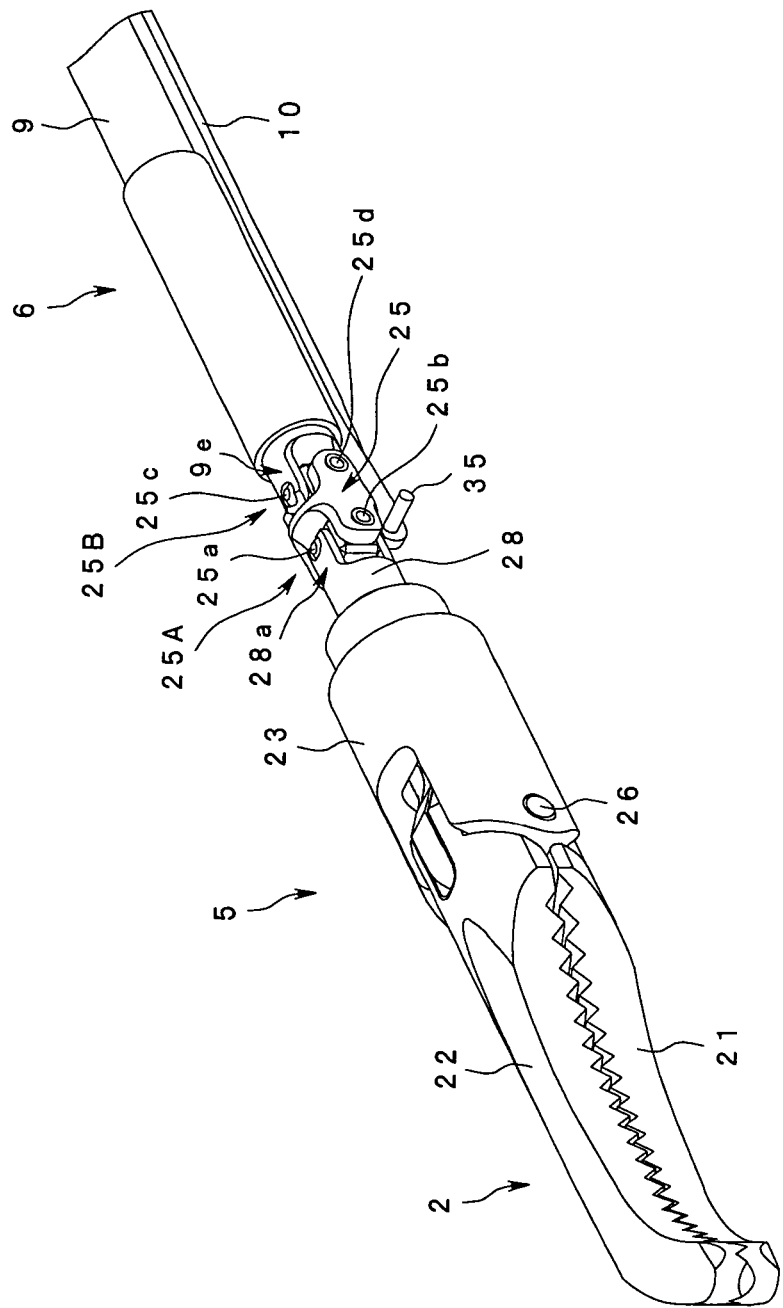
FIG. 8 is diagram which shows the construction in a state in which the unit attachment and detachment member, pivoting base, distal end cover and insertion tube are removed from the treatment part unit and insertion tube unit in a connected state.

Accordingly, projecting part 9e and 28a whose cross-sectional shapes are formed substantially as U shapes (as shown in FIG. 8 described later), and which act as connecting parts that connect with the joint member 25, are respectively formed in the distal end portion of the treatment part operating rod 9 and the proximal end portion of the connecting member 28.

Figure 4:
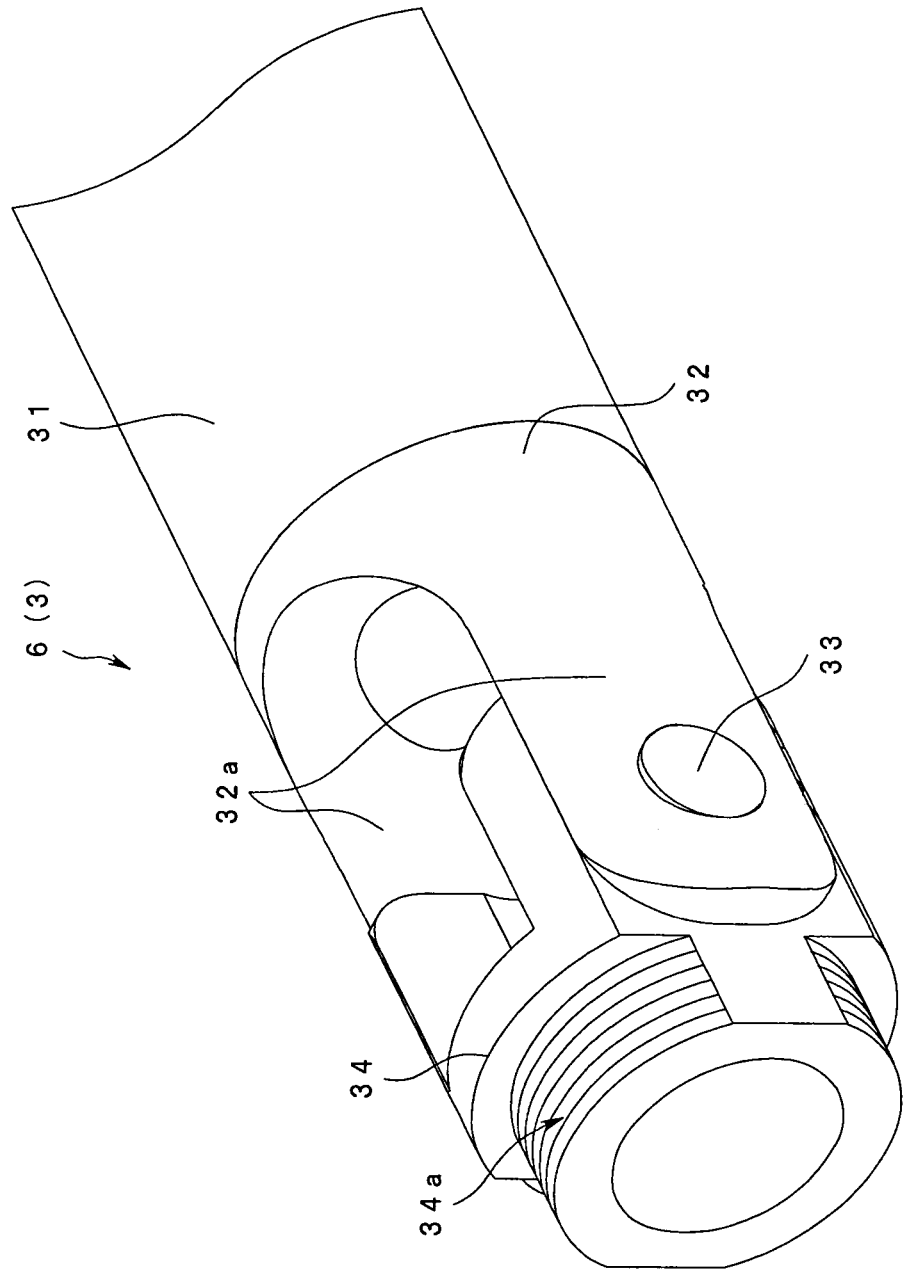
FIG. 4 is a diagram which illustrates the construction of the distal end portion of the insertion tube unit.

As is shown in FIGS. 2 and 4, the insertion tube unit 6 is constructed mainly from an insertion tube 30 that constitutes the insertion part 3, and a distal end cover 32. The second knob 12 and third knob 13 are disposed on the proximal end portion of the insertion tube 30.

The distal end cover 32 is fastened to the distal end opening part of the insertion tube 30. The distal end of this distal end cover 32 is formed as a projecting part 32a whose cross-sectional shape is substantially a U shape. A tubular pivoting base 34 is disposed inside this projecting part 32a. The pivoting base 34 is connected via a pair of pivoting base pivoting pins 33 constituting a pivoting shaft so that this base is free to pivot. Furthermore, a male screw part 34a that is screw-engaged with the female screw part 24a is formed on the distal end portion of this pivoting base 34.

Furthermore, a pivoting base operating rod (described later) is inserted through the interior of the insertion tube 30 so that this rod is free to advance and retract. The pivoting base operating rod is a member which is used to pivot the pivoting base 34. The pivoting base operating rod is a rigid member, and is formed with a specified length dimension. The distal end portion of this pivoting base operating rod is connected to a specified position on the pivoting base 34 so that the rod is free to pivot (as will be described later).

Figure 5:
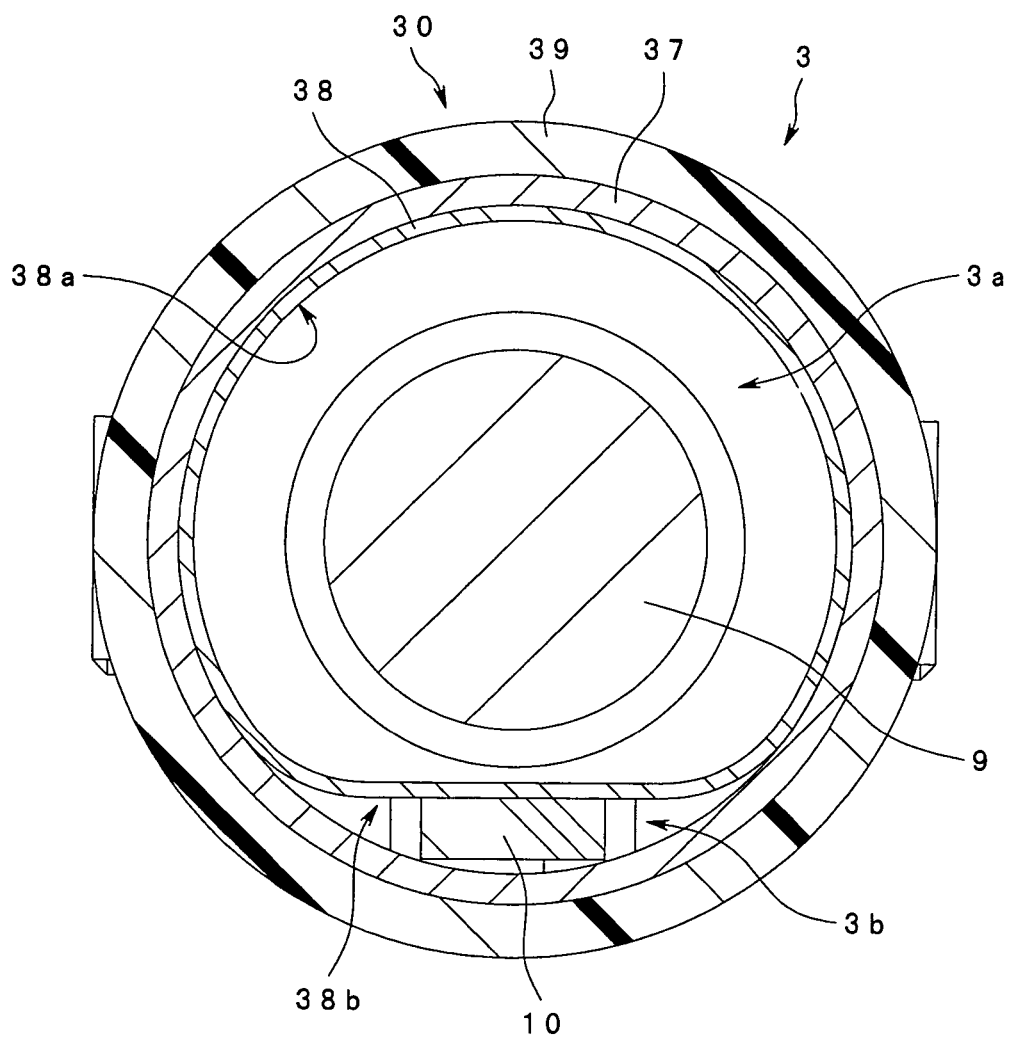
FIG. 5 is a sectional view along line 5-5 in FIG. 1.

As is shown in FIG. 5, the insertion tube 30 that constitutes the insertion part 3 is constructed from a main body tube part 37, a region forming tube 38, and an insulating covering 39. The main body tube part 37 is an elongated tubular member that possesses rigidity, and is formed by (for example) a stainless steel member. The region forming tube 38 is a region forming member that divides the internal hole of this main body tube part 37 into a plurality of regions. Like the main body tube part 37, this region forming tube 38 is an elongated tubular member which possesses rigidity, and has a cross-sectional shape that is formed as a specified shape. The insulating covering 39 covers the main body tube part 37.

The region forming tube 38 of the present embodiment has an outer circumferential curved surface part 38a that is formed with a curved surface, and a rectilinear part 38b that is formed with a rectilinear shape. The outer circumferential curve surface part 38a is disposed so that this part adheres tightly to the inner circumferential surface of the main body tube part 37.

The treatment part operating rod 9 is disposed in a first space 3a which is an internal space in the region forming tube 38 so that this rod can freely advance and retract in the axial direction. This treatment part operating rod 9 constitutes an opening-and-closing link mechanism which opens and closes the treatment part 2 constituted by the first treatment piece 21 and second treatment piece 22.

Meanwhile, a pivoting base operating rod 10 is disposed in a second space 3b which is an internal space formed by the outer surface of the rectilinear part 38b of the region forming tube 38 and the inner circumferential surface of the main body tube part 37. This pivoting base operating rod 10 constitutes a pivoting link mechanism which varies the pivoting angle of the treatment part 2 with respect to the direction of the longitudinal axis of the insertion part within the range of the angle θ (described later). The cross-sectional shape of this pivoting base operating rod 10 is formed as a rectangular shape.

Specifically, the treatment part operating rod 9 and the pivoting base operating rod 10 are disposed parallel to the axial direction inside specified spaces inside the insertion part 3. Furthermore, the treatment part operating rod 9 and the pivoting base operating rod 10 are disposed so that these rods can freely advance and retract inside the insertion part 3. Moreover, as is shown in FIG. 5, the treatment part operating rod 9 is disposed in substantially the center of the insertion part 3, while the pivoting base operating rod 10 is disposed (for example) in a position that is offset downward from the center of the insertion part 3.

Furthermore, the opening shape of the second space 3b is formed with consideration given to the cross-sectional shape, and especially the thickness dimension, of the pivoting base operating rod 10. This pivoting base operating rod 10 has a relatively small thickness dimension, and is long and slender in the direction of length; however, this rod is formed so that buckling can be prevented and the transmission of force in the axial direction can be reliably accomplished when such force is transmitted by the advancing or retracting movement of this rod in the axial direction.

Furthermore, in the present embodiment, the region forming member is formed by a region forming tube 38, i.e., a tubular member. However, this region forming member is not limited to a tubular member, and may be (for example) a plate member or the like. Specifically, a construction in which a plate member of specified dimensions is disposed in the internal hole of the main body tube part 37 so that respective spaces are formed, and a treatment part operating rod 9 and pivoting base operating rod 10 formed with specified cross-sectional shapes are inserted and disposed inside these spaces, may be used.

Figure 6:
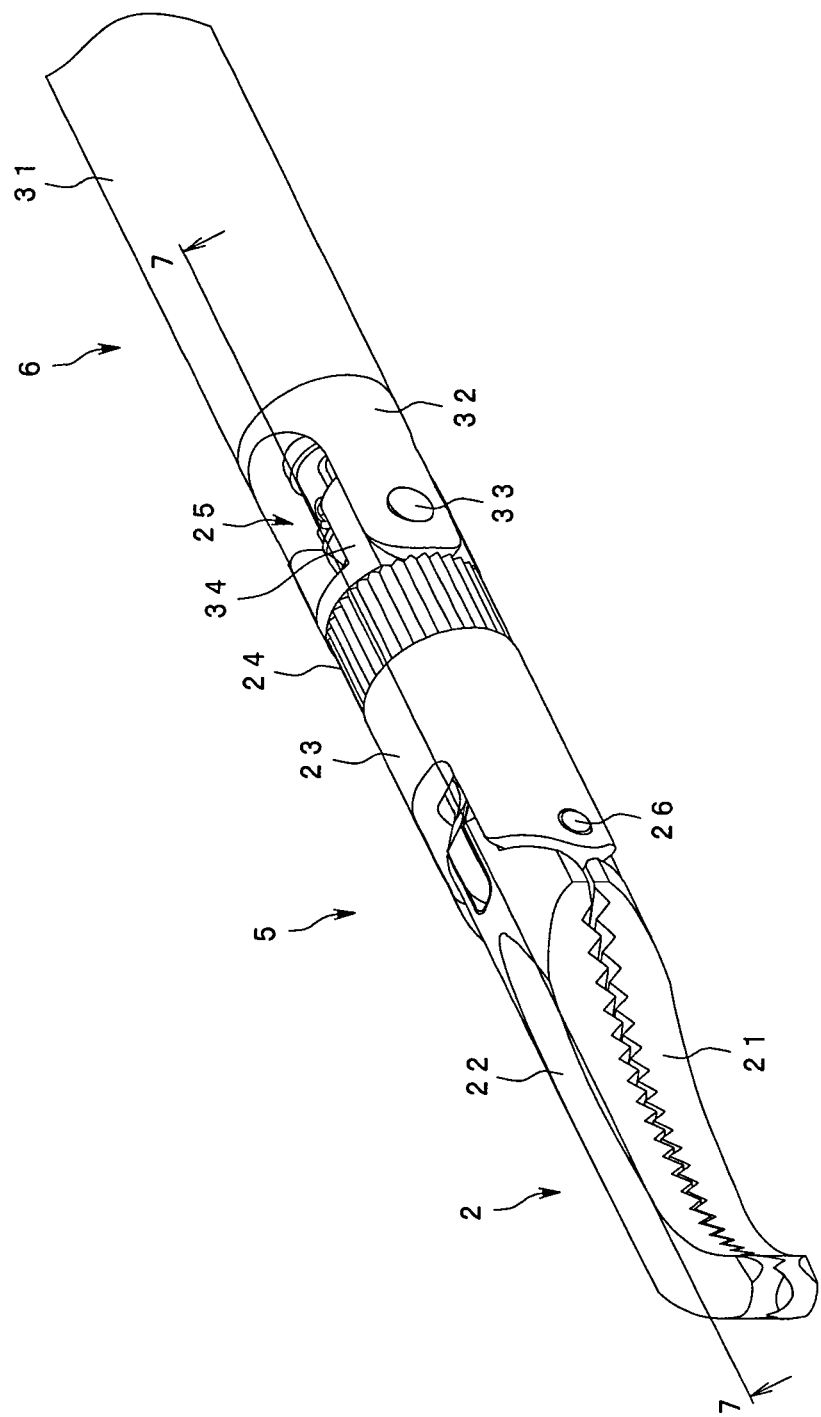
FIG. 6 is a diagram which shows the distal end portions of the treatment part unit and insertion tube unit in a connected and fastened state.
Figure 7:
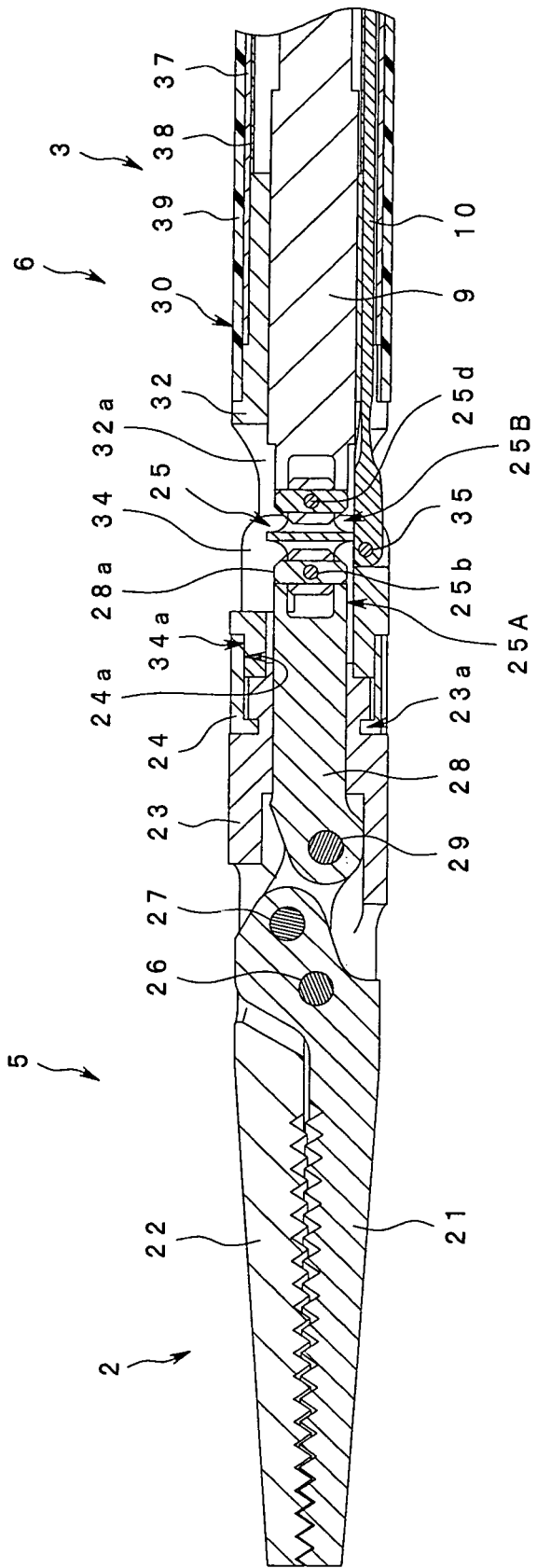
FIG. 7 is a sectional view along line 7-7 in FIG. 6.

As is shown in FIGS. 6 and 7, the distal end portion of the treatment part unit 5 and the distal end portion of the insertion tube unit 6 are integrally connected and fastened in a state in which the treatment part operating rod 9 is inserted and disposed inside the first space 3a of the insertion tube 30.

This unit attachment and detachment member 24 is constructed by inserting and disposing a projecting part 24b formed on this unit attachment and detachment member 24 into a recessed part 23a formed in the proximal end portion of the treatment part base 23 so that free pivoting is possible.

Accordingly, when the unit attachment and detachment member 24 is rotated in a specified direction so that the female screw part 24a and the male screw part 34a are screw-engaged, the unit attachment and detachment member 24 is screwed into and fastened to the pivoting base 34. In this state, the treatment part base 23 is held in a state that allow rotation about the axis with respect to the pivoting base 34.

Furthermore, when the unit attachment and detachment member 24 is rotated in the opposite direction in this screw-fastened state, the screw-engaged state of the female screw part 24a and the male screw part 34a is released. Consequently, the treatment part unit 5 and the insertion tube unit 6 can be separated.

Furthermore, although this is not shown in the drawings, when the treatment part unit 5 and insertion tube unit 6 are placed in a screw-fastened state, the proximal end portion of the treatment part operating rod 9 and the rotational driving rod 9b protrude by a specified amount from the proximal end surface of the insertion tube unit 6.

As is shown in FIG. 7, the distal end portion of the pivoting base operating rod 10 is connected to a specified position on the pivoting base 34 so that this rod is free to pivot. The distal end portion of the pivoting base operating rod 10 is connected to a specified position on the pivoting base 34 by a pivoting base operating rod distal end holding pin (hereafter abbreviated to "pivoting holding pin") 35. This pivoting holding pin 35 is disposed in a parallel positional relationship with respect to the pivoting base pivoting pin 33.

Meanwhile, an intermediate portion of the first treatment piece 21 is supported on the distal end of the treatment part base 23 via a first treatment piece opening-and-closing pin 26 so that this first treatment piece 21 is free to pivot. Furthermore, the proximal end portion of the first treatment piece 21 and the intermediate portion of the second treatment piece 22 are supported via a treatment part pivoting pin 27 so that free pivoting is possible. This treatment part pivoting pin 27 is disposed in a parallel positional relationship with the first treatment piece opening-and-closing pin 26. As a result, a construction is formed in which the first treatment piece 21 and the second treatment piece 22 are free to pivot relative to each other with the treatment part pivoting pin 27 as a supporting point.

The second treatment piece 22 that constitutes a part of the treatment part 2 and the treatment part operating rod 9 are connected via a connecting member 28 having rigidity that is formed in a substantially cylindrical shape, and the joint member 25. In concrete terms, the distal end portion of this connecting member 28 and the proximal end portion of the second treatment piece 22 are connected by a connecting pin 29 so that free pivoting is possible. Furthermore, the projecting part 28a of this connecting member 28 and the projecting part 9e of the treatment part operating rod 9 are connected by the joint member 25 so that free pivoting is possible (as will be described later). Moreover, the connecting pin 29 is also in a parallel positional relationship with the first treatment piece opening-and-closing pin 26.

As is shown in FIGS. 7 and 8, the projecting part 28a of the connecting member 28 and the distal end of the joint member 25 are respectively by a first joint pin 25a and a second joint pin 25b so that free pivoting is possible.

Furthermore, the proximal end of the joint member 25 and the projecting part 9e of the treatment part operating rod 9 are respectively connected by a third joint pin 25c and a fourth joint pin 25d so that free pivoting is possible. The third joint pin 25c is in a parallel positional relationship with the first joint pin 25a. Furthermore, the fourth joint pin 25d is in a parallel positional relationship with the second joint pin 25b.

In other words, the joint member 25 has a construction comprising two sets of universal joints known as so-called Cardan couplings or cross couplings.

Furthermore, the outer circumferential surface of the treatment part operating rod 9 is devised so that the treatment part operating rod 9 can advance and retract in the direction of the longitudinal axis constituting the main axis of the insertion part 3 while this outer circumferential surface contacts the inner circumferential surface of the distal end cover 32. Moreover, the outer circumferential surface of the connecting member 28 is also constructed so that this surface contacts the inner circumferential surface of the treatment part base 23.

As a result of this construction, the connecting member 28 advances and retracts along the axial direction of the treatment part base 23. Furthermore, when the treatment part operating rod 9 is caused to pivot, the joint member 25 and connecting member 28 pivot inside the distal end cover 32 and pivoting base 34. Moreover, the connecting pin 29, second treatment piece 22, treatment part pivoting pin 27, first treatment piece 21, first treatment piece opening-and-closing pin 26 and treatment part base 23 connected to the connecting member 28 pivot about the distal end cover 32 and pivoting base 34.

The first universal joint 25A and the second universal joint 25B are constructed so that these joints can transmit a pivoting motion in a range in which the pivoting axes before and after the respective universal joints 25A and 25B form an angle of 45 degrees. Furthermore, the first universal joint 25A is positioned on the distal end side of the joint member 25 constructed from the first joint pin 25a, second joint pin 25b and the like, and the second universal joint 25B is positioned on the proximal end side of the joint member constructed from the third joint pin 25c, fourth joint pin 25d and the like.

Furthermore, in the present embodiment, as is shown in FIG. 1 and FIGS. 6 through 8, the first treatment piece 21 and second treatment piece 22 that constitute the treatment part 2 are in a closed state in a state in which the distal end portion of the treatment part operating rod 9 is disposed furthest on the proximal end side. This closed state will be referred to as the first terminating state. The instrument is constructed so that in this closed state, the center point of the first universal joint 25A and the central axis of the pivoting base pivoting pin 33 coincide.

Figure 13:
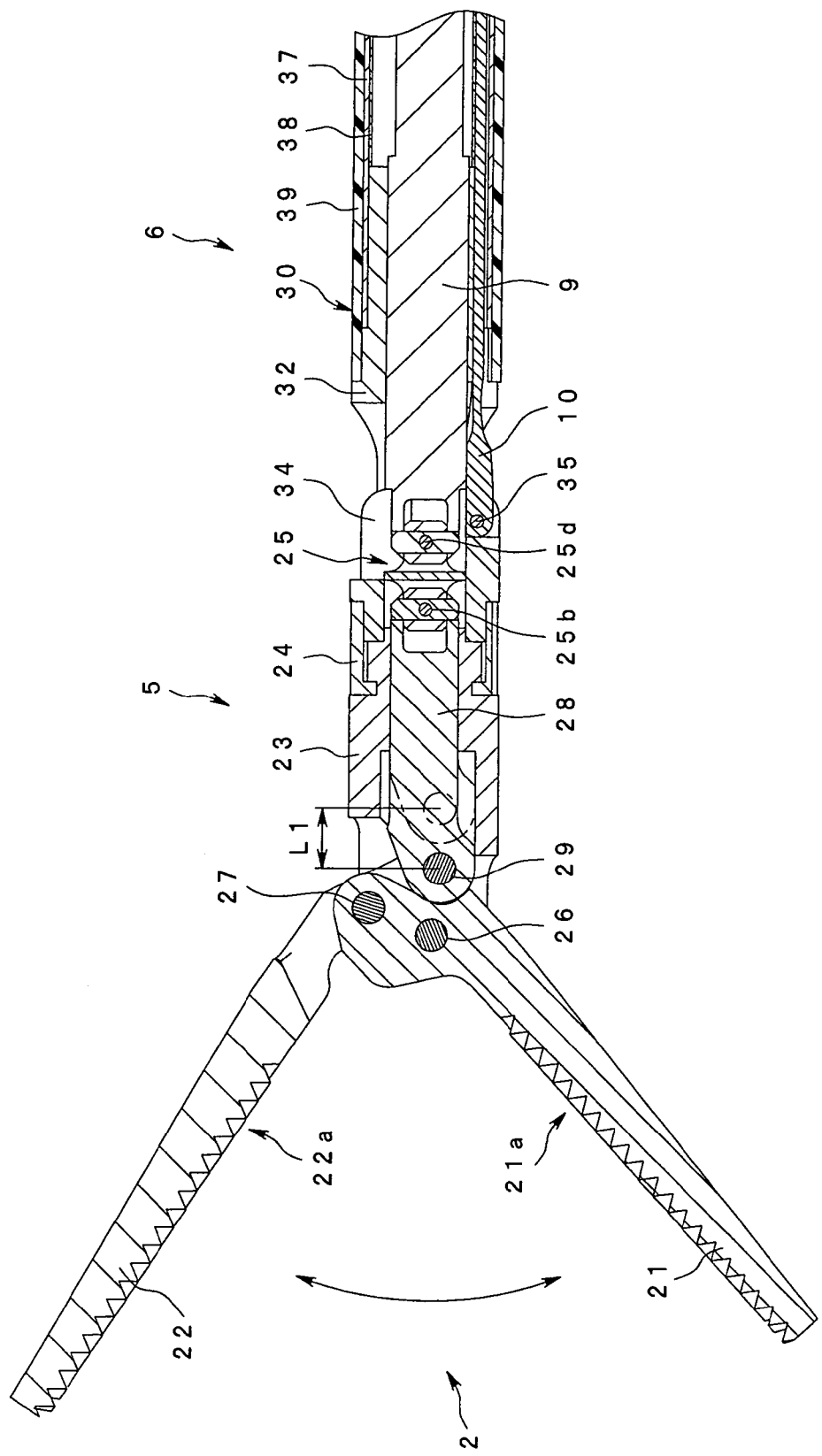
FIG. 13 is a diagram which illustrates the relationship between the movement of the connecting pin and the opening-and-closing operation of the first treatment piece and second treatment piece.

Meanwhile, in a state in which the distal end portion of the treatment part operating rod 9 is moved and disposed furthest toward the distal end side as shown in FIG. 13 (described later), the first treatment piece 21 and second treatment piece 22 that constitute the treatment part 2 are in a maximum open state. This maximum open state will be referred to as the second terminating state. In this case, the joint member 25, the connecting member 28 and the proximal end portion of the second treatment piece 22 are moved to the furthest distal end side. The instrument is constructed so that in this maximum open state, the center point of the second universal joint 25B and the central axis of the pivoting base pivoting pin 33 coincide.

In other words, in the present embodiment, the spacing between the center point of the first universal joint 25A of the joint member 25 and the center point of the second universal join 25B is set so that the above-mentioned relationships are established.

Furthermore, for example, roulette working or the like which has an anti-slip function is performed on the outer circumferential surface of the unit attachment and detachment member 24 so that the pivoting operation can be performed easily and reliably.

Furthermore, as is shown in FIG. 13, a gripping surface 21a and a gripping surface 22a that face each other are formed on the first treatment piece 21 and the second treatment piece 22. Working that forms indentations and projections or the like is performed as necessary on these gripping surfaces 21a and 22a. As a result, living tissues or the like that are the object of gripping can be securely gripped by the gripping surfaces 21a and 22a.

Furthermore, the first treatment piece 21 and second treatment piece 22 are not limited to dissection forceps with the shape shown in the drawings; these treatment parts may comprise dissection forceps, scissors, grasping forceps or the like constructed with any desired shape.

Figure 9:
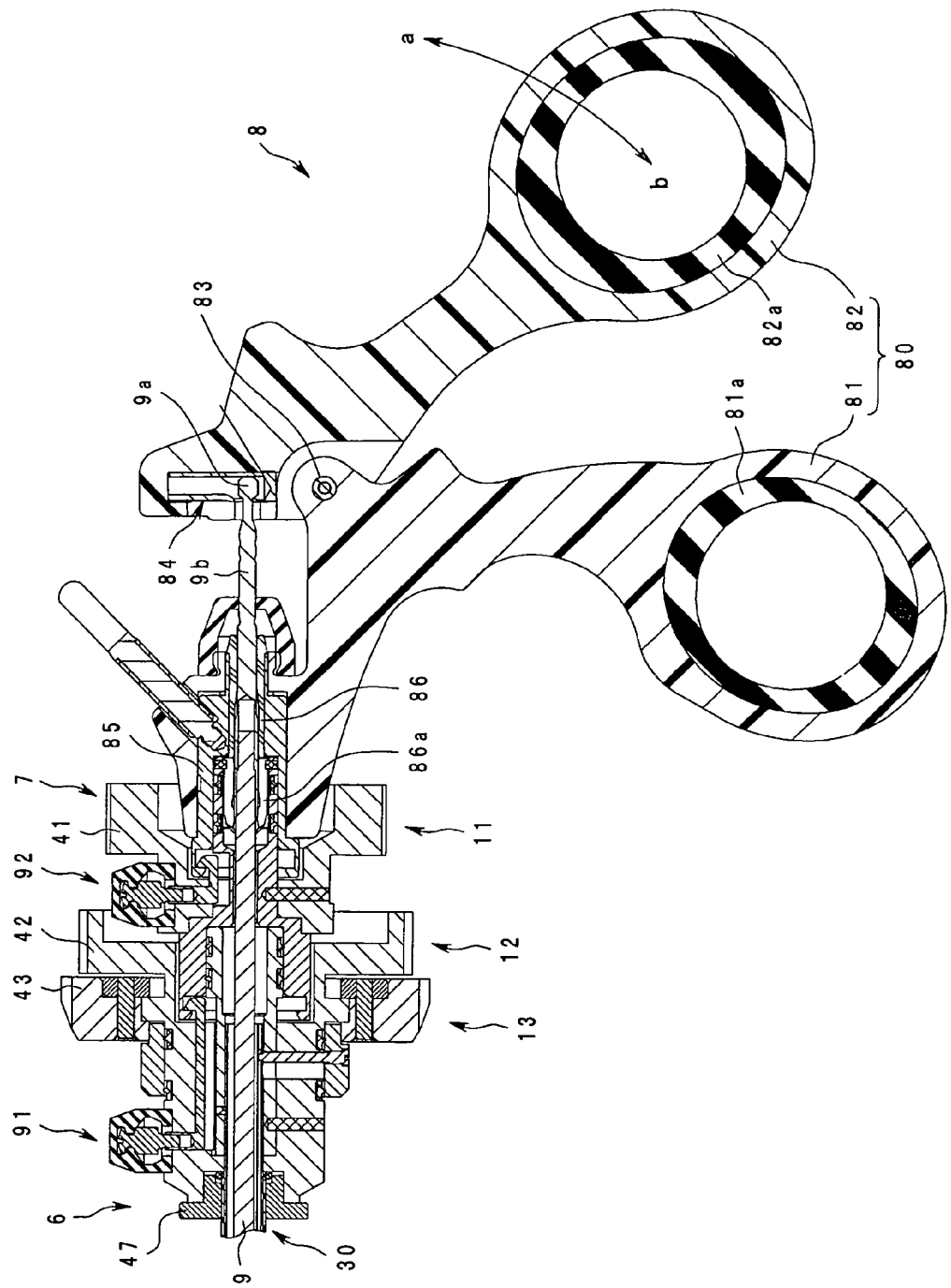
FIG. 9 is a diagram which shows the construction of the proximal end portion of the insertion tube unit, and the constructions of the treatment part rotating unit disposed on the proximal end portion of this insertion tube unit and the gripping operating unit disposed on this treatment part rotating unit.

As is shown in FIGS. 2 and 9, a first attachment and detachment mechanism part 91 comprising a release mechanism 91 is disposed on the second knob 12. The treatment part pivoting unit 7 comprising the first knob 11 is constructed so that this unit can be freely attached to or detached from the proximal end portion of the insertion tube unit 6 via this first attachment and detachment mechanism part 91.

Furthermore, a second attachment and detachment mechanism part 92 comprising a release mechanism is disposed on the first knob 11. The gripping operating unit 8 has a construction which allows attachment to and detachment from the insertion tube unit 6 via this second attachment and detachment mechanism part 92.

Here, the constructions of the attachment and detachment mechanism parts 91 and 92 will first be concretely described.

Figure 10:
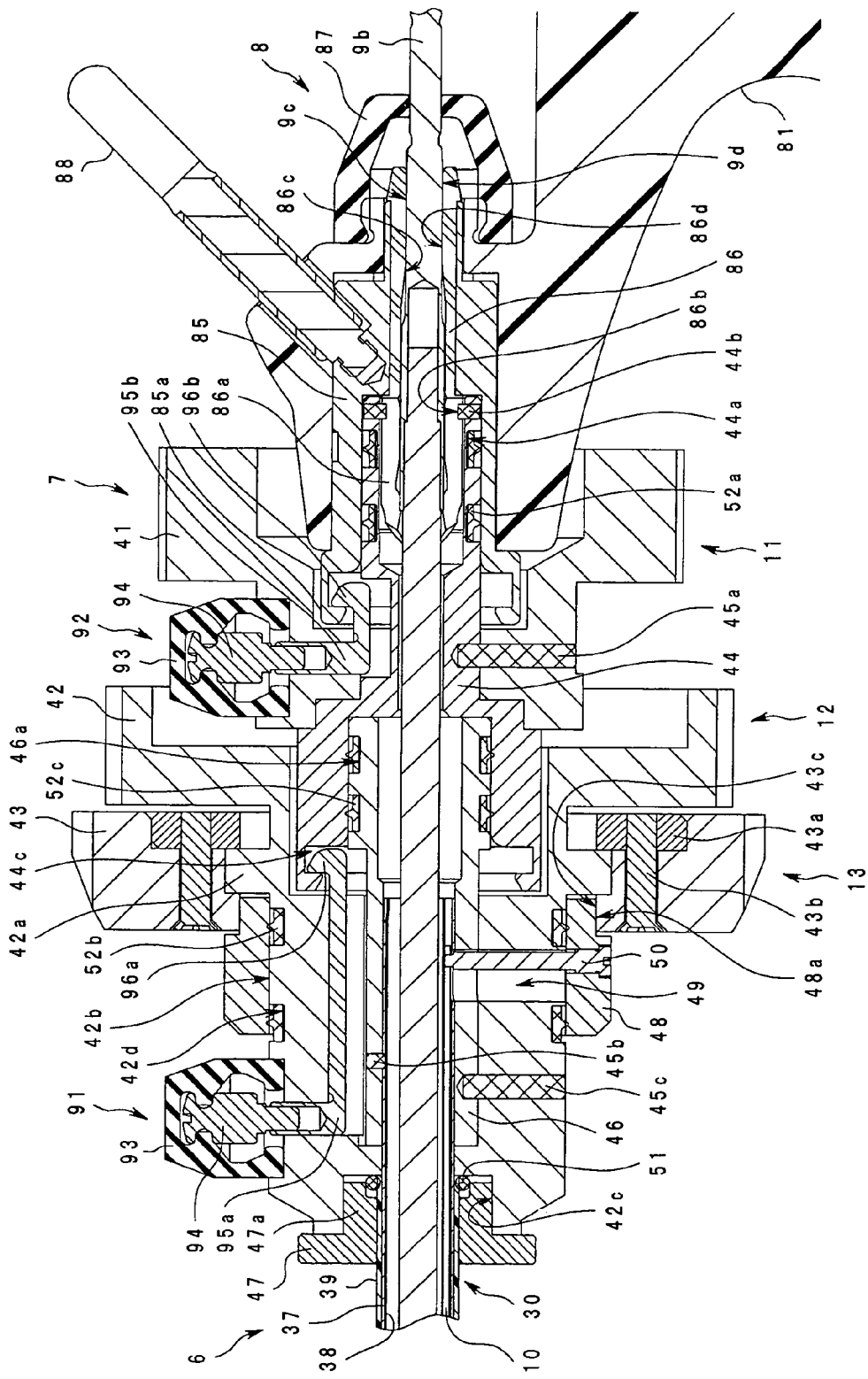
FIG. 10 is an enlarged view which concretely illustrates the construction of the main parts in FIG. 9.

As is shown in FIG. 10, the first attachment and detachment mechanism part 91 and the second attachment and detachment mechanism part 92 are each constructed from a button part 93, a button shaft 94 and a pawl member 95 which has a specified shape. The button part 93 is formed by an elastic member. The button shaft 94 possesses rigidity, and the button part 93 is disposed on this button shaft 94. The pawl member 95 is integrally fastened to the distal end portion of the button shaft 94 by screw engagement.

The pawl member 95 of the first attachment and detachment mechanism part 91 and the pawl member 95 of the second attachment and detachment mechanism part 92 have different shapes. In the present drawings, the pawl member of the first attachment and detachment mechanism part 91 is indicated by the symbol 95a, and the pawl member of the second attachment and detachment mechanism part 92 is indicated by the symbol 95b.

When the pawl members 95a and 95b of the attachment and detachment mechanism parts 91 and 92 are in a state in which these members are not pressed by the fingers of the operator, i.e., an unloaded state, this results in a state in which the pawl members 95a and 95b are moved upward by the elastic force of the button parts 93.

Then, in this state, when the operator presses the button parts 93 against the elastic force of these parts, the button shafts 94 are moved downward (in the drawings). As a result, the pawl members 95a and 95b that are integrally attached to these button shafts 94 are moved downward.

When the operator again removes his/her fingers from the button parts 93 in this pressed state, the button shafts 94 are moved upward (in the drawings) by the elastic force of the button parts 93. In this case, the pawl members 95a and 95b are also moved upward in the same manner as the button shafts 94.

Next, the construction of the gripping operating unit 8 will be described with reference to FIGS. 9 and 10.

The gripping operating unit 8 is constructed mainly from a fixed handle 81 and a pivoting handle 82 that constitute the treatment part opening-and-closing operating part 80.

Through-holes through which the fingers of the user are inserted are formed in specified positions in this fixed handle 81 and pivoting handle 82. Rings 81a and 82a are respectively disposed in these through-holes. These rings 81a and 82a are disposed in order to reduce the load on the fingers during operation.

The fixed handle 81 and the pivoting handle 82 are shaft-supported via a handle pin 83 so that these handles are free to pivot. Accordingly, the pivoting handle 82 can pivot in the direction indicated by the arrow a and the direction indicated by the arrow b in the drawings about the handle pin 83.

A driving rod bearing 84 in which the ball part 9a of the rotational driving rod 9b is detachably disposed with free play is formed in a specified part on the distal end side of the pivoting handle 82. As a result of the ball 9a being inserted and disposed in this driving rod bearing 84, the rotational driving rod 9b is held in a state that allows this rod to pivot relative to the driving rod bearing 84.

Meanwhile, a handle base 85 is disposed on the distal end portion of the fixed handle 81. The handle base 85 constitutes a part that can be attached to and detached from the second attachment and detachment mechanism part 92 disposed on the treatment part rotating unit 7. An engaging part 85a is disposed on the distal end portion of this handle base 85. The pawl part 96b of the pawl member 95b constituting the second attachment and detachment mechanism part 92 is engaged with the engaging part 85a.

A driving rod bearing 86 is inserted and disposed in the internal hole of the handle base 85 so that this bearing can pivot about the axis. This driving rod bearing 86 is substantially tubular. A guide part 86a that is long and slender in the axial direction is formed on the distal end portion of this driving rod bearing 86. For example, the distal end portions of a pair of rotation transmitting guide pins 44b disposed on the proximal end portion of a first knob base (described later; see symbol 44) are respectively inserted and engaged in this guide part 86a.

Contact planes 86c and 86d are formed in the internal hole of the driving rod bearing 86. Planar parts 9c and 9d formed on the side surface parts of the rotational driving rod 9b are disposed so that these parts contact these contact planes 86c and 86d.

Accordingly, if the driving rod bearing 86 is rotated in a state in which the rotational driving rod 9b is inserted and disposed inside the driving rod bearing 86, the treatment part operating rod 9 rotates in accordance with the rotation of the driving rod bearing 86. In other words, the treatment part operating rod 9 has a construction which is such that the rod 9 rotates 360 degrees in accordance with the pivoting of the driving rod bearing 86.

An air-tight cap 87 is disposed on the fixed handle 81. This air-tight cap 87 adheres tightly to the side circumferential surface of the rotational driving rod 9b that protrudes toward the driving rod bearing 84. As a result, a drop in the pressure inside the abdominal cavity that might result from a state of communication between the first space 3a and second space 3b and the outside during the surgical procedure is prevented. Furthermore, the symbol 88 indicates a high-frequency input pin that is disposed on the fixed handle 81.

Next, the construction of the treatment part rotating unit 7 will be described with reference to FIG. 10.

The treatment part rotating unit 7 is constructed mainly from a tubular first knob main body 41 and a first knob base 44. The first knob main body 41 forms the first knob 11.

The first knob base 44 is integrally fastened to the first knob main body 41 by a first knob connecting member 45a in a state in which the knob base 44 is inserted and disposed in the hole part of the first knob main body 41. Rotation transmitting guide pins 44b are disposed on the proximal end portion of the first knob base 44. These rotation transmitting guide pins 44b are inserted and disposed in the guide part 86a. In this inserted and disposed state, the driving rod bearing 86 and the first knob base 44 are in a state that allows integral rotation.

Accordingly, the first knob main body 41 is pivoted in a state in which the rotation transmitting guide pin 44b is inserted and disposed in the guide part 86a. Consequently, the first knob base 44, driving rod bearing 86 and rotational driving rod 9b move in linkage with the pivoting action of the first knob main body 41, so that the treatment part operating rod 9 is caused to pivot.

Furthermore, the second attachment and detachment mechanism part 92 is disposed in a specified position on the first knob main body 41 that constitutes the treatment part rotating unit 7. Moreover, a circumferential groove 44a is formed in a specified position in the proximal end portion of the first knob base 44. A first air-tight seal 52a is disposed in the circumferential groove 44a. The first air-tight seal 52a maintains air-tightness between the first knob base 44 and the handle base 85.

Next, the construction of the proximal end portion of the insertion tube unit 6 will be described with reference to FIG. 10.

The second knob 12 which is integrally disposed on the insertion tube 30 is constructed mainly from a tubular second knob main body 42 which forms the second knob 12, a second knob base 46, and a knob distal end cover member 47. A tubular third knob main body 43 which forms the third knob 13, and an advancing and retracting member 48 which is integrally disposed on the third knob main body 43 in a screw-engaged state, are disposed on the second knob main body 42.

The second knob base 46 is fastened to a specified position on the proximal end portion of the insertion tube 30 via a base connecting member 45b. The second knob main body 42 is integrally fastened to the second knob base 46 via a second knob connecting member 45c. As a result, the second knob 12 is disposed in a specified position on the proximal end portion of the insertion tube 30.

Accordingly, when the second knob main body 42 is caused to pivot, the second knob base 46 moves in linkage with the pivoting action of the second knob main body 42, so that the insertion tube 30 performs a pivoting action.

A flange part 42a and a trunk part 42b are formed in the second knob main body 42. The third knob main body 43 is disposed on the flange part so that the third knob main body 43 is free to pivot. The advancing and retracting member 48 is disposed on the trunk part 42b so that the member 48 is free to advance and retract in the axial direction, and the first attachment and detachment mechanism part 91 is disposed thereon.

A through-hole 49 with a specified diameter dimension is formed in a specified position in the trunk part 42b of the second knob main body 42 and the second knob base 46. This through-hole 49 allows access to the proximal end portion of the pivoting base operating rod 10 that is inserted and disposed in the second space 3b. A connecting and fastening screw 50 is disposed inside this through-hole 49. This connecting and fastening screw 50 integrally connects and fastens the proximal end portions of the advancing and retracting member 48 and the pivoting base operating rod 10.

The third knob main body 43 is disposed by means of a third knob retainer 43a and a fastening screw 43b so that the third knob main body 43 can pivot relative to the flange part 42a of the second knob main body 42. A female screw part 43c is formed in the inner circumferential surface on the distal end side of the third knob main body 43. Meanwhile, a male screw part 48a that engages with the female screw part 43c is formed on the proximal end portion of the advancing and retracting member 48. Furthermore, this third knob main body 43 is disposed in a specified position on the trunk part 42b of the second knob main body 42 in a state in which the male screw part 48a of the advancing and retracting member 48 and the female screw part 43c of the third knob main body 43 are screw-engaged.

Accordingly, when the third knob main body 43 which is disposed on the second knob main body 42 so that the third knob main body 43 is free to pivot is caused to perform a pivoting operation, the state of screw engagement of the female screw part 43c and male screw part 48a varies. Consequently, the advancing and retracting member 48 advances or retracts in the axial direction on the trunk part 42b. Furthermore, in linkage with the axial advancing or retracting movement of the advancing and retracting member 48, the pivoting base operating rod 10 that is integrally connected and fastened to the advancing and retracting member 48 via the connecting and fastening screw 50 is caused to perform an advancing or retracting movement.

A distal end recessed part 42c is formed in the distal end portion of the second knob main body 42. The distal end portion 47a of the knob distal end cover member 47 is disposed in the distal end recessed part. An O-ring 51 that possesses a specified elastic force is disposed inside the distal end recessed part 42c.

The O-ring 51 is constructed so that this O-ring is pressed by the distal end surface of the knob distal end cover member 47. Furthermore, when the O-ring 51 is pressed by the distal end surface of the knob distal end cover member 47, the O-ring deforms so that the O-ring expands in the direction of diameter. As a result, the O-ring 51 is placed in a state in which the O-ring adheres tightly to the insulating covering 39 that constitutes a part of the insertion tube 30. As a result, the fastened state of the knob distal end cover member 47 to the insertion tube 30 is made secure.

A pair of circumferential recessed parts 42d are formed in the outer circumferential surface of the trunk part 42b on which the advancing and retracting member 48 is disposed, which is the outer circumferential side that is faced by the through-hole 49. Second air-tight seals 52b which maintain the air-tightness between the outer circumferential surface of the trunk part 42b and the inner circumferential surface of the advancing and retracting member 48 are disposed in these circumferential recessed parts. These second air-tight seals 52b prevent a drop in the internal pressure of the abdominal cavity that might be caused by a state of communication between the second space 3b and the outside via the through-hole 49.

When the treatment part rotating unit 7 is integrally connected with the insertion tube unit 6, the inner circumferential surface of the first knob base 44 is disposed on the outer circumferential surface of the proximal end portion of the second knob base 46. Furthermore, circumferential grooves 46a are formed in the proximal end portion of the second knob base 46. Third air-tight seals 52c which maintain the air-tightness between the outer circumferential surface of the second knob base 46 and the inner circumferential surface of the first knob base 44 are disposed in these circumferential grooves 46a.

Furthermore, the diameter dimensions of the first knob 11, second knob 12 and third knob 13 are formed so that these diameter dimensions expand toward the distal end side from the side of the treatment part opening-and-closing operating part 80 in order to improve the operating characteristics.

Furthermore, an engaging recessed part 44c is formed in the distal end portion of the first knob base 44. The pawl part 96a of the pawl member 95a that constitutes the first attachment and detachment mechanism part 91 is detachably engaged with this engaging recessed part 44c.

Furthermore, for example, working that forms indentations and projections that have an anti-slip function is performed on the outer circumferential surfaces that constitute the pivoting operating parts of the first knob main body 41, second knob main body 42 and third knob main body 43. As a result of the provision of this working that forms indentations and projections, the pivoting operation performed by the fingers of the operator can be performed easily and reliably.

Furthermore, for example, the surgical instrument shown in the FIG. 1 is constructed by assembling the insertion tube unit 6 and treatment part rotating unit 7, and then attaching the gripping operating unit 8 to this treatment part rotating unit 7.

In this case, the treatment part rotating unit 7 disposed on the proximal end portion of the insertion tube unit 6 is engaged with the handle base 85 of the gripping operating unit 8, and the ball part 9a of the rotational driving rod 9b that is an integral part of the treatment part operating rod 9 that constitutes the treatment part unit 5 is inserted and disposed in the driving rod bearing 84.

Next, the operation of the surgical instrument 1 constructed as described above will be described.

The surgical instrument 1 is constructed so that the treatment part 2 can be caused to perform specified operations by appropriately operating the treatment part opening-and-closing operating part 80, first knob 11, second knob 12 and third knob 13 with the hands.

Below, the relationship between the manual operation of the treatment part opening-and-closing operating part 80, first knob 11, second knob 12 and third knob 13 and the operation of the treatment part 2 will be described with reference to the attached drawings.

First, the operation that is performed in a case where the treatment part opening-and-closing operating part is operated alone will be described.

Figure 11:
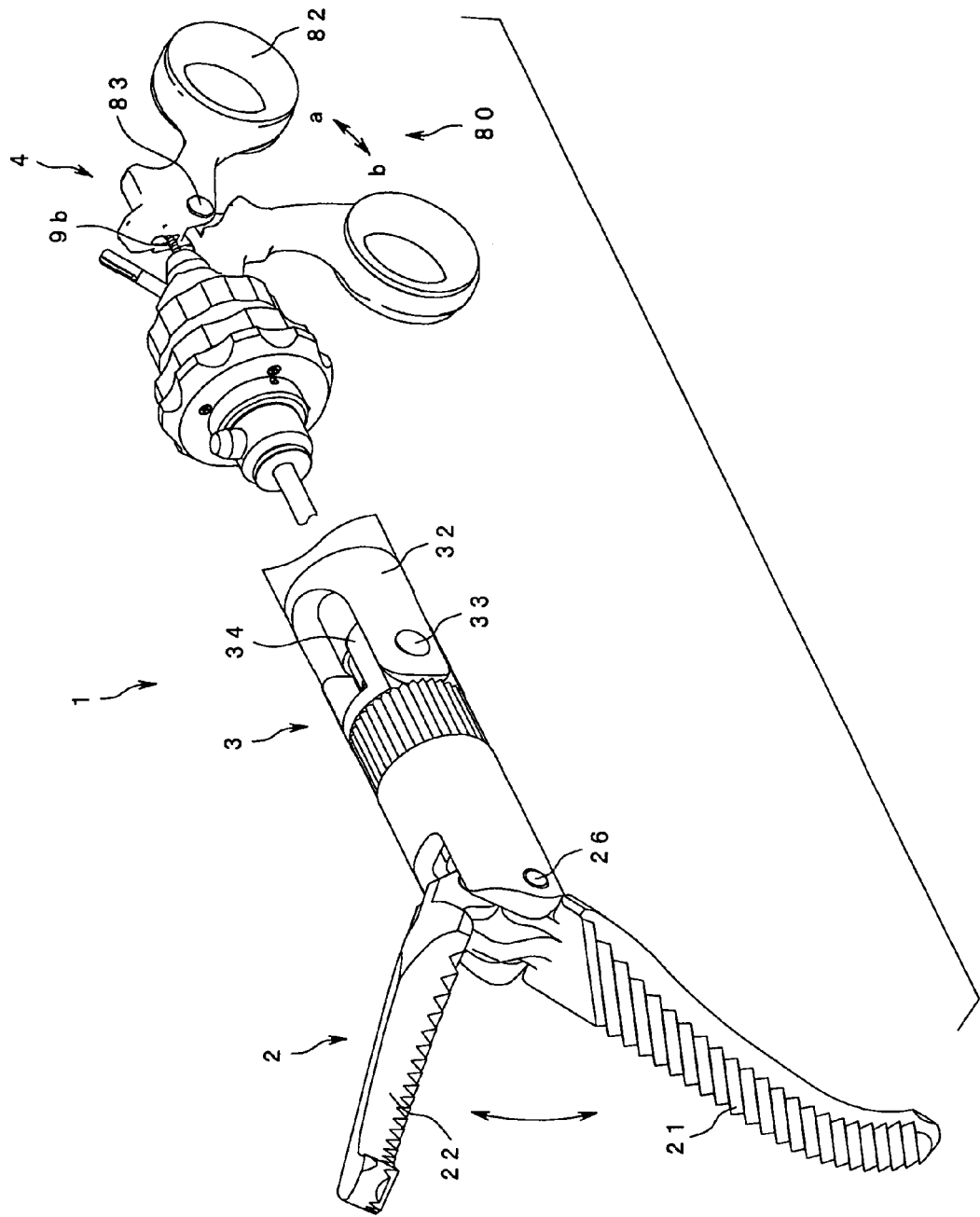
FIG. 11 is a diagram which illustrates the relationship between the operation of the pivoting handle and the opening-and-closing operation of the first treatment piece and second treatment piece that constitute the treatment part.

The pivoting handle 82 of the treatment part opening-and-closing operating part 80 of the surgical instrument 1 in the state shown in FIG. 1 is moved in the direction indicated by the arrow a in FIG. 11. As a result, the first treatment piece 21 and second treatment piece 22 that constitute the treatment part 2 of the surgical instrument 1 change from a closed state to an open state. Furthermore, if the pivoting handle 82 is moved in the direction indicated by the arrow b in this open state, the first treatment piece 21 and second treatment piece 22 that were in an open state change to a closed state.

Figure 12:
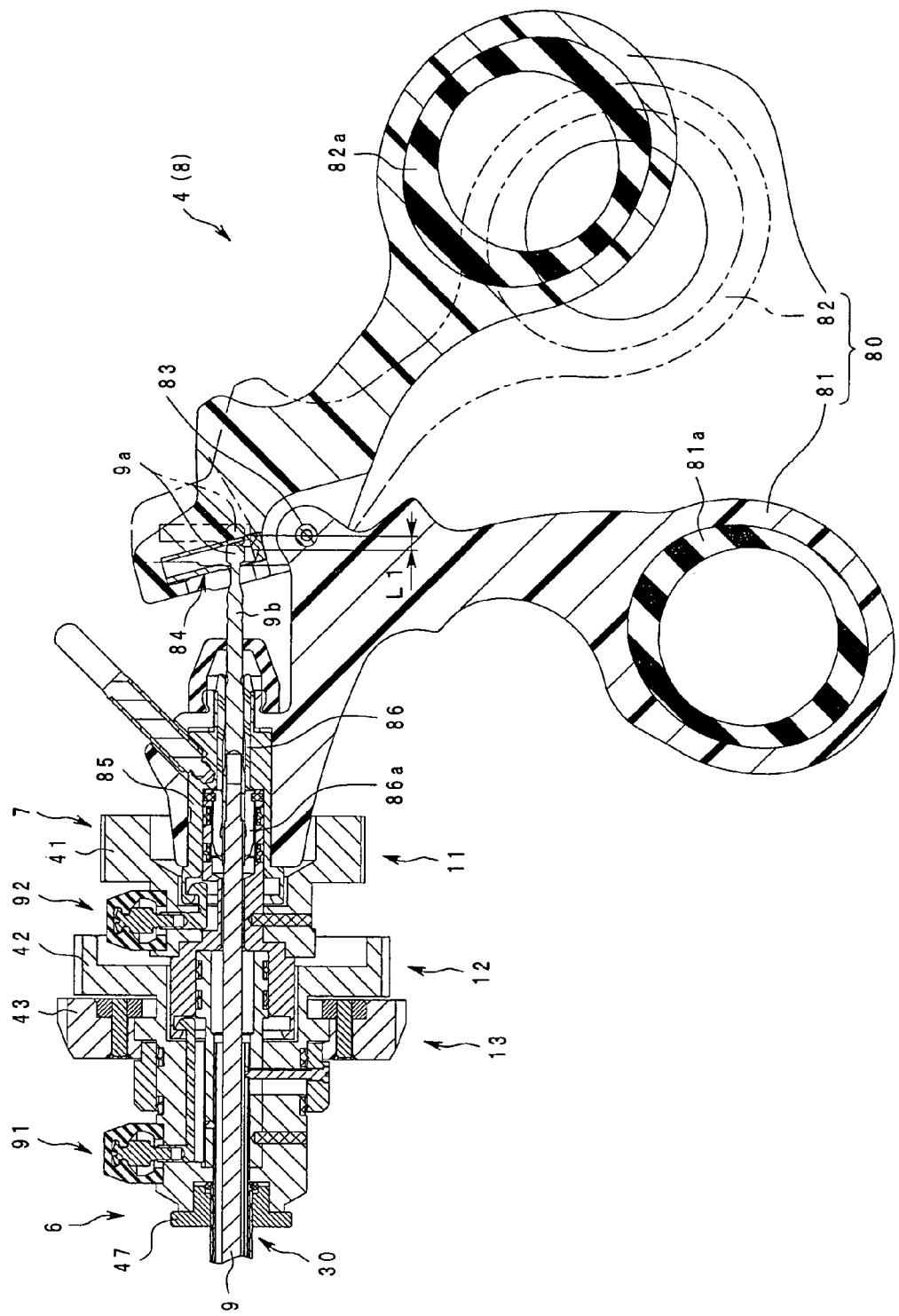
FIG. 12 is a diagram which illustrates the relationship between operation of the pivoting handle and the movement variation state of the ball part.
Figure 14:
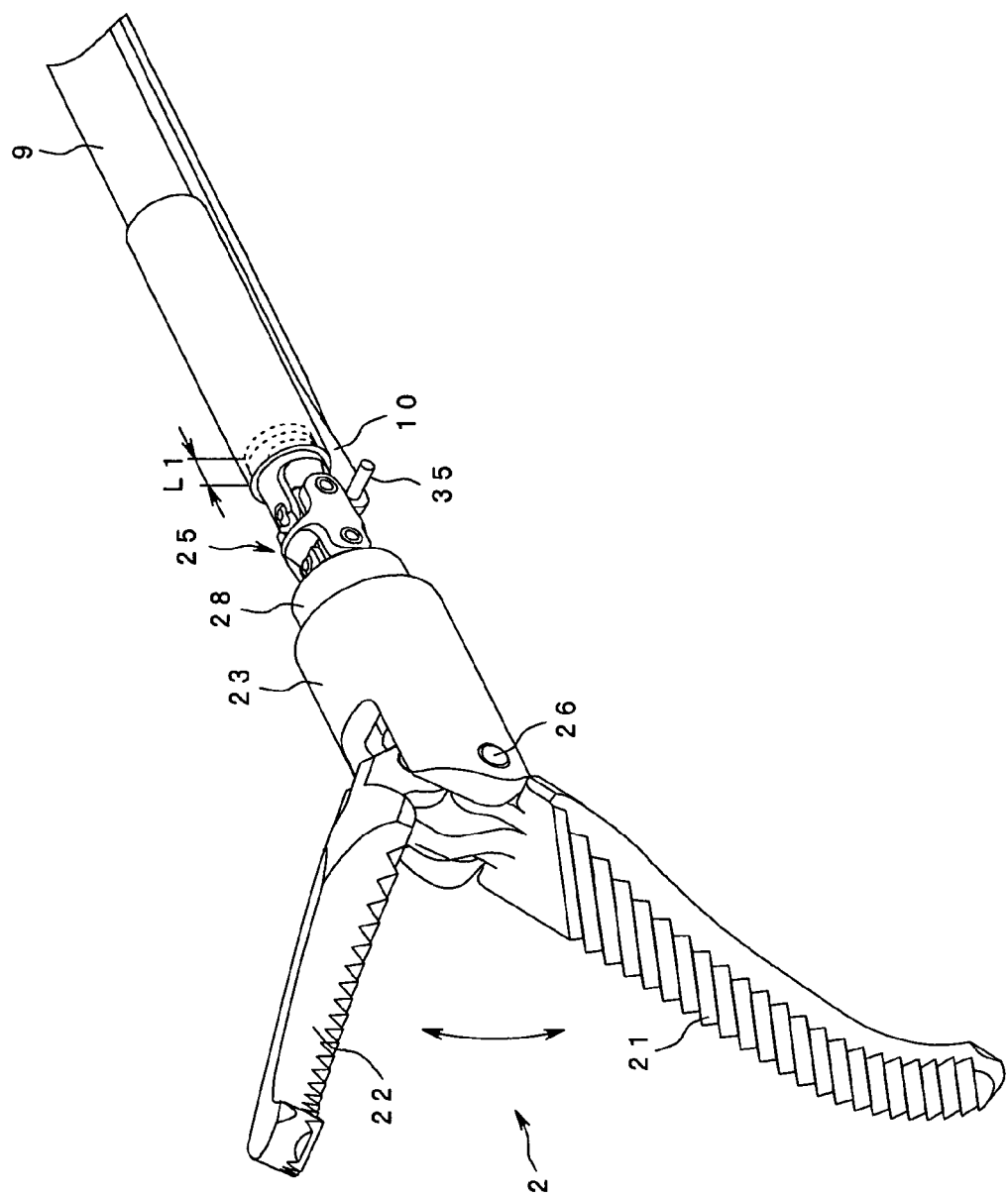
FIG. 14 is a diagram which illustrates the relationship between the movement of the distal end portion of the treatment part operating rod and the opening-and-closing operation of the first treatment piece and second treatment piece.

In concrete terms, as is shown in FIG. 12, the pivoting handle 82 is caused to pivot from the position indicated by the one-dot chain line to the position indicated by the solid line. Consequently, the ball part 9a moves parallel to the direction of the longitudinal axis of the surgical instrument 1 by a distance of L1. As a result, the treatment part operating rod 9 also performs a parallel movement by a distance of L1 as shown in FIGS. 13 and 14. Furthermore, in linkage with the movement of this treatment part operating rod 9, the joint member 25 and the connecting pin 29 disposed on the connecting member 28 also perform a parallel movement for a distance of L1. Consequently, the first treatment piece 21 and second treatment piece 22 that constitute the treatment part 2 move relative to each other and perform an opening and closing action as shown by the arrows in the drawing.

Next, the operation that is performed when the third knob 13 is operated alone will be described.

Figure 15:
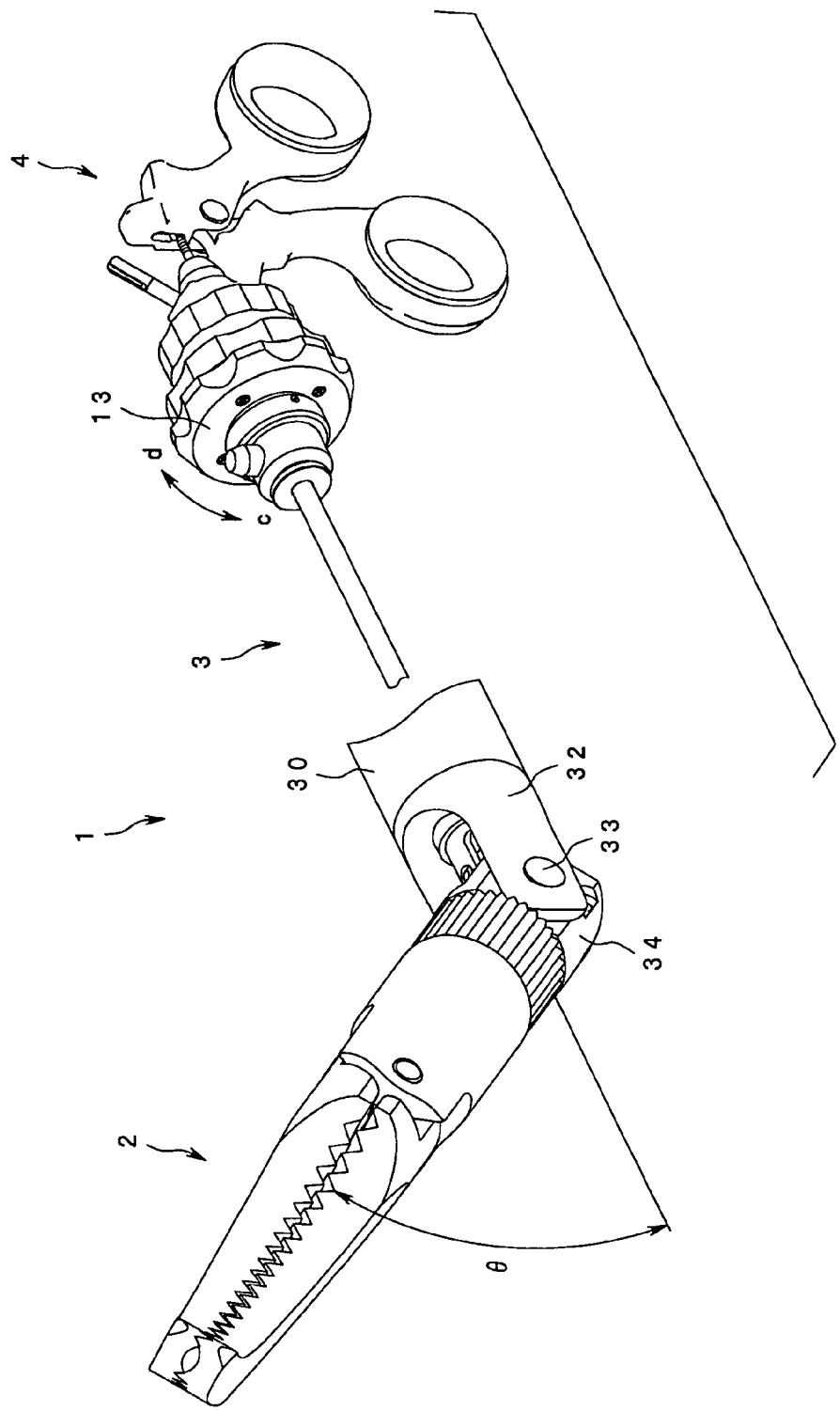
FIG. 15 is a diagram which illustrates the relationship between the pivoting operation of the third knob and the pivoting state of the treatment part.

The third knob 13 of the surgical instrument 1 in the state shown in the FIG. 1 is caused to pivot in the direction indicated by the arrow c as shown in FIG. 15. As a result, the treatment part 2 that was disposed in a horizontal position with respect to the longitudinal axis of the surgical instrument 1 changes to a state in which this treatment part 2 is inclined by an angle of $\theta$ with respect to this longitudinal axis. Then, in this state in which the treatment part 2 is inclined by an angle of $\theta$, the third knob 13 is rotated in the direction indicated by the arrow d. Consequently, the treatment part 2 moves toward the longitudinal axis, i.e., the angle of inclination varies so that the angle $\theta$ is reduced.

Furthermore, the instrument may also be constructed so that the treatment part 2 is inclined by an angle of $\theta$ as a result of the operation of the third knob 13 in the direction indicated by the arrow d, and so that the angle $\theta$ is reduced by the rotation of the third knob 13 in the direction indicated by the arrow c.

Figure 16:
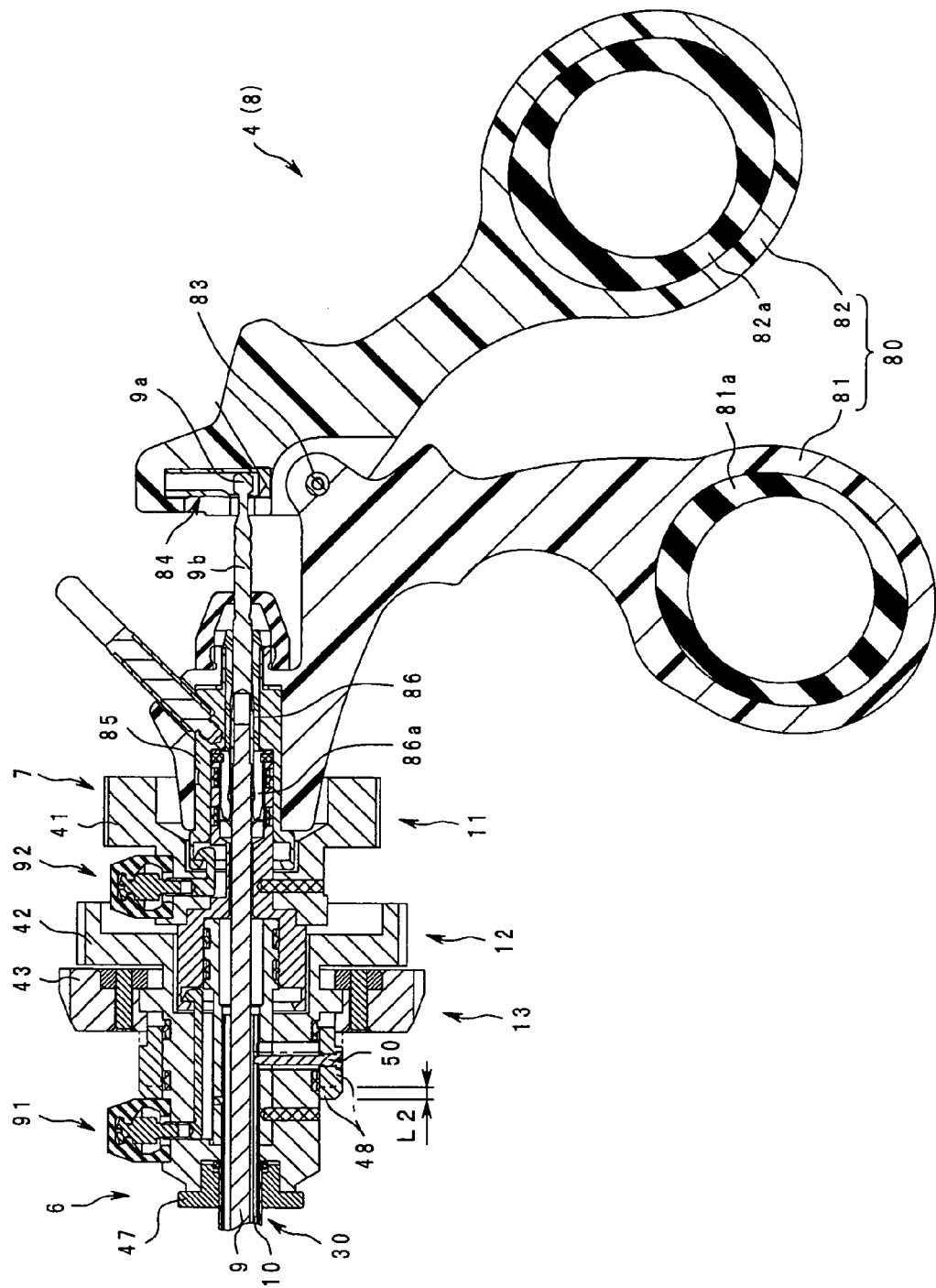
FIG. 16 is a diagram which illustrates the relationship between the pivoting operation of the third knob and the movement variation state of the connecting and fastening screw.

In concrete terms, the third knob 13 is rotated in the direction indicated by the arrow c or the direction indicated by the arrow d. As a result, the advancing and retracting member 48 moves by a distance of L2 over the trunk part 42b of the second knob main body 42 from the position indicated by the one-dot chain line to the position indicated by the solid line as shown in FIG. 16. Furthermore, the male screw part 48a of the advancing and retracting member 48 and the female screw part 43c of the third knob main body 43 on which the third knob 13 is formed are in a screw-engaged state.

As a result, the pivoting base operating rod 10 which is integrally connected and fastened to the advancing and retracting member 48 by the connecting and fastening screw 50 also moves parallel to the direction of the longitudinal axis of the surgical instrument 1 by a distance of L2.

Figure 17:
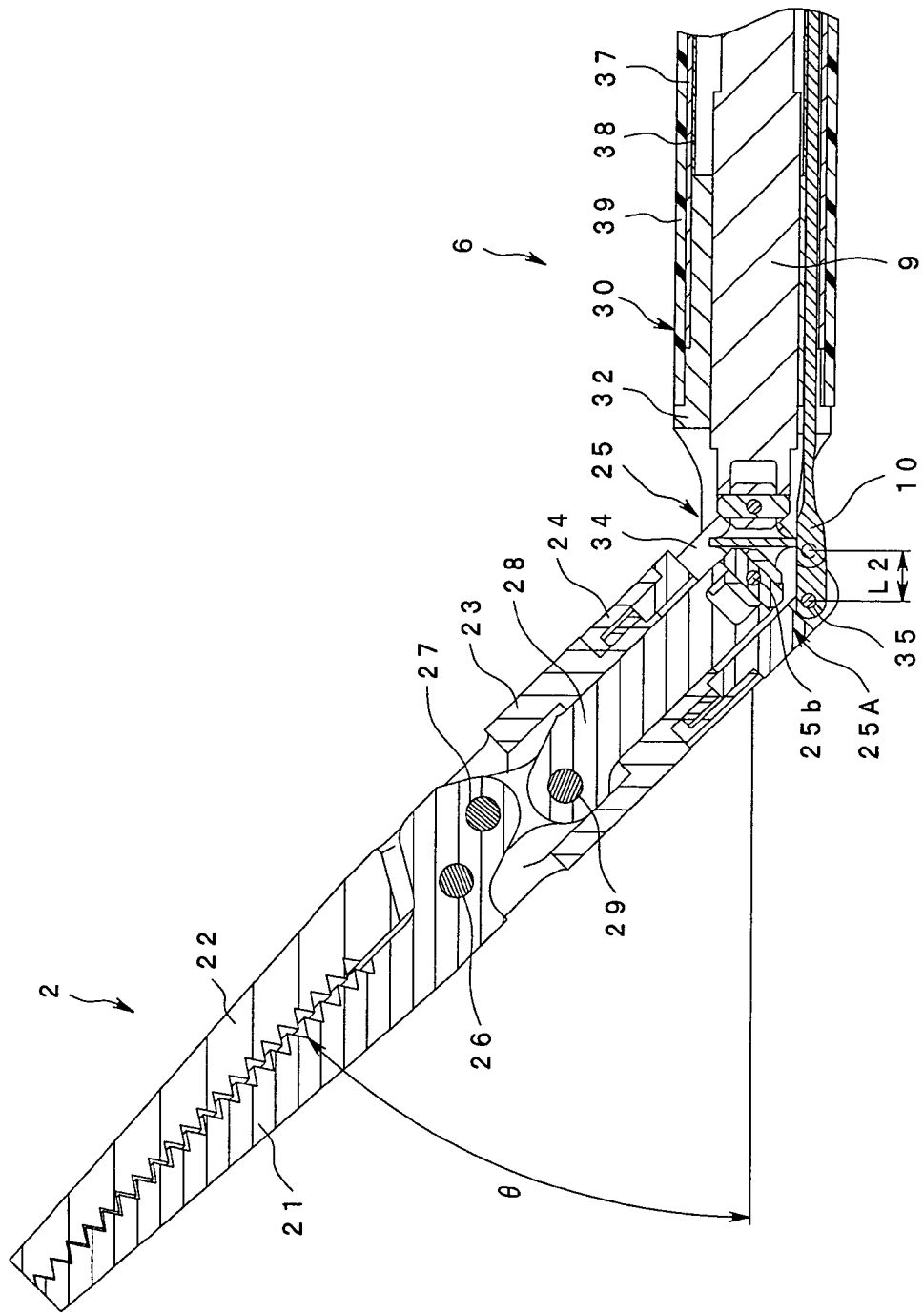
FIG. 17 is a diagram which illustrates the relationship between the movement of the distal end portion of the pivoting base operating rod and the pivoting state of the treatment part.
Figure 18:
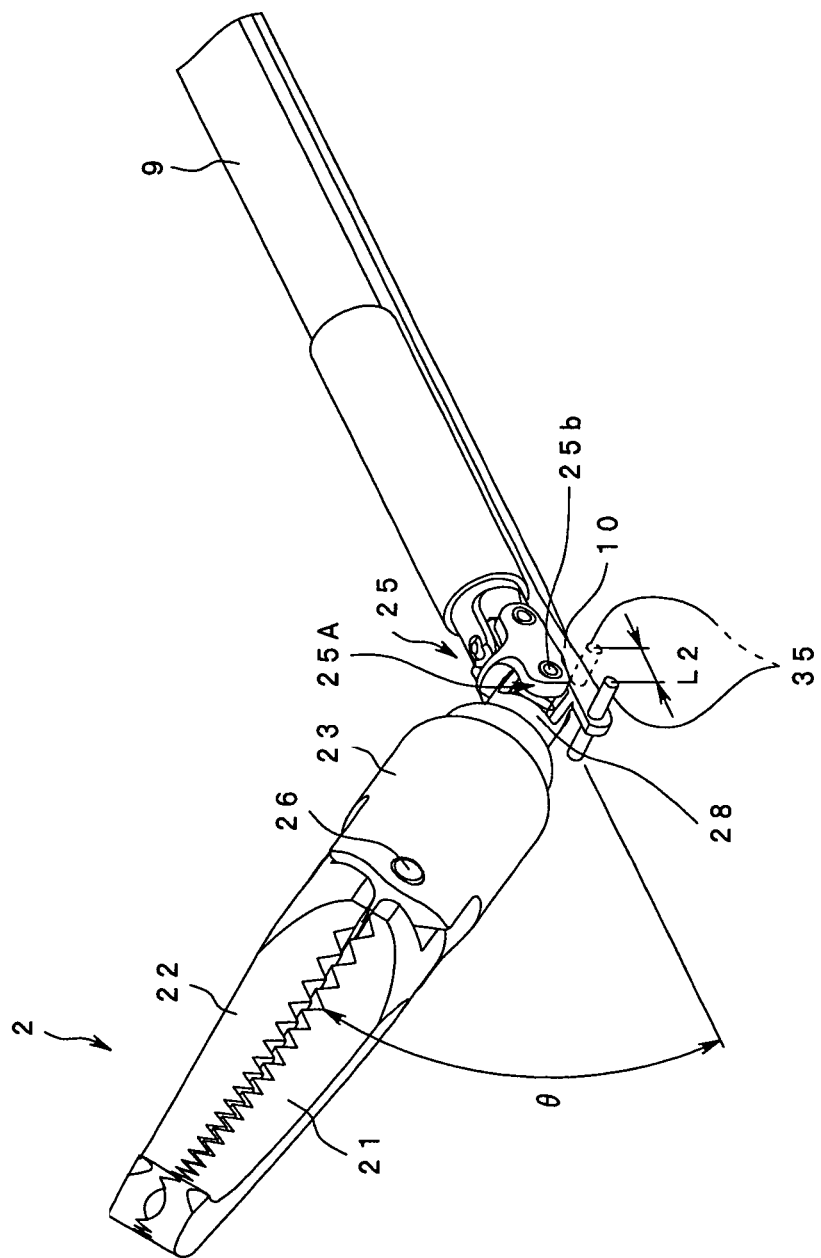
FIG. 18 is a diagram which illustrates the relationship between the movement state of the pivoting base operating rod and the bent state of the joint member.

Consequently, the pivoting holding pin 35 that is positioned on the distal end portion of the pivoting base operating rod 10 performs a parallel movement by a distance of L2 as shown in FIGS. 17 and 18. Accordingly, an action whereby the pivoting base 34 pivots about the pivoting base pivoting pin 33 is caused to take place.

As a result, the treatment part 2 pivots upward (in the drawings) through a specified angular range from a position parallel to the direction of the longitudinal axis of the surgical instrument 1.

In this case, since the connecting member 28 pivots through a range of 0 degrees to 45 degrees about the second joint pin 25b of the joint member 25, the treatment part 2 performs a pivoting action through a range that is inclined by 45 degrees from a horizontal state with respect to the direction of the longitudinal axis of the surgical instrument 1.

Next, the operation that is performed when the second knob 12 is operated alone will be described.

The second knob 12 of the surgical instrument 1 in the state shown in the FIG. 1 is caused to pivot. As a result, the insertion tube 30 that is integrally disposed on this second knob 12 rotates in the direction of the pivoting operation. In this case, the distal end cover 32 that is fastened to the distal end portion of the insertion tube 30 also rotates in the same manner as the insertion tube 30. Consequently, the pivoting base 34 that is attached to this distal end cover 32 via the pivoting base pivoting pin 33 also similarly rotates.

In other words, as a result of the pivoting operation of the second knob 12, the distal end cover 32 and pivoting base 34 are caused to pivot together with the insertion tube 30. Accordingly, the pivoting direction of the pivoting base 34 that is disposed on the distal end cover 32 via the pivoting base pivoting pin 33 so that this pivoting base 34 is free to pivot can be set at a desired orientation by turning the second knob 12.

Next, the operation that is performed when the first knob 11 is operated alone will be described.

Figure 19:
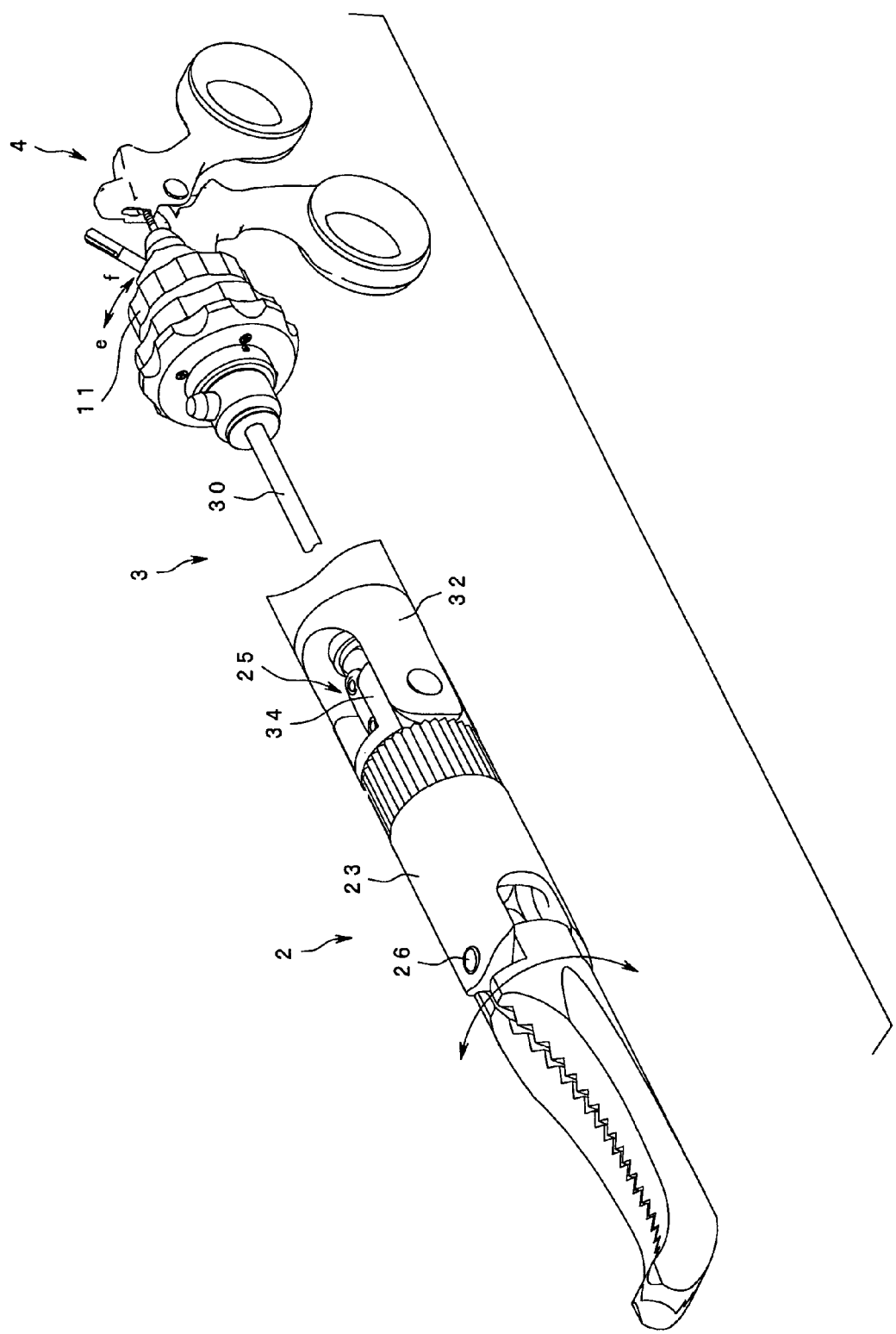
FIG. 19 is a diagram which illustrates the relationship between the pivoting operation of the first knob and the swiveling state of the treatment part.

The first knob 11 of the surgical instrument 1 in the state shown in the FIG. 1 is rotated in the direction indicated by the arrow e as shown in FIG. 19. As a result, the treatment part 2 is rotated about the longitudinal axis of the surgical instrument 1. Consequently, the first treatment piece opening-and-closing pin 26 disposed on the treatment part base 23 changes (for example) from a state facing toward the front in FIG. 6 to a state facing upward in FIG. 19. Furthermore, in this state, the first knob 11 is rotated in the direction indicated by the arrow f. As a result, the treatment part 2 rotates in the opposite direction about the longitudinal axis of the surgical instrument 1. In other words, in response to the pivoting operation of the first knob 11, the treatment part base 23 is caused to pivot as indicated by the arrows, so that the treatment part 2 swivels about the longitudinal axis of the surgical instrument 1.

Figure 20:
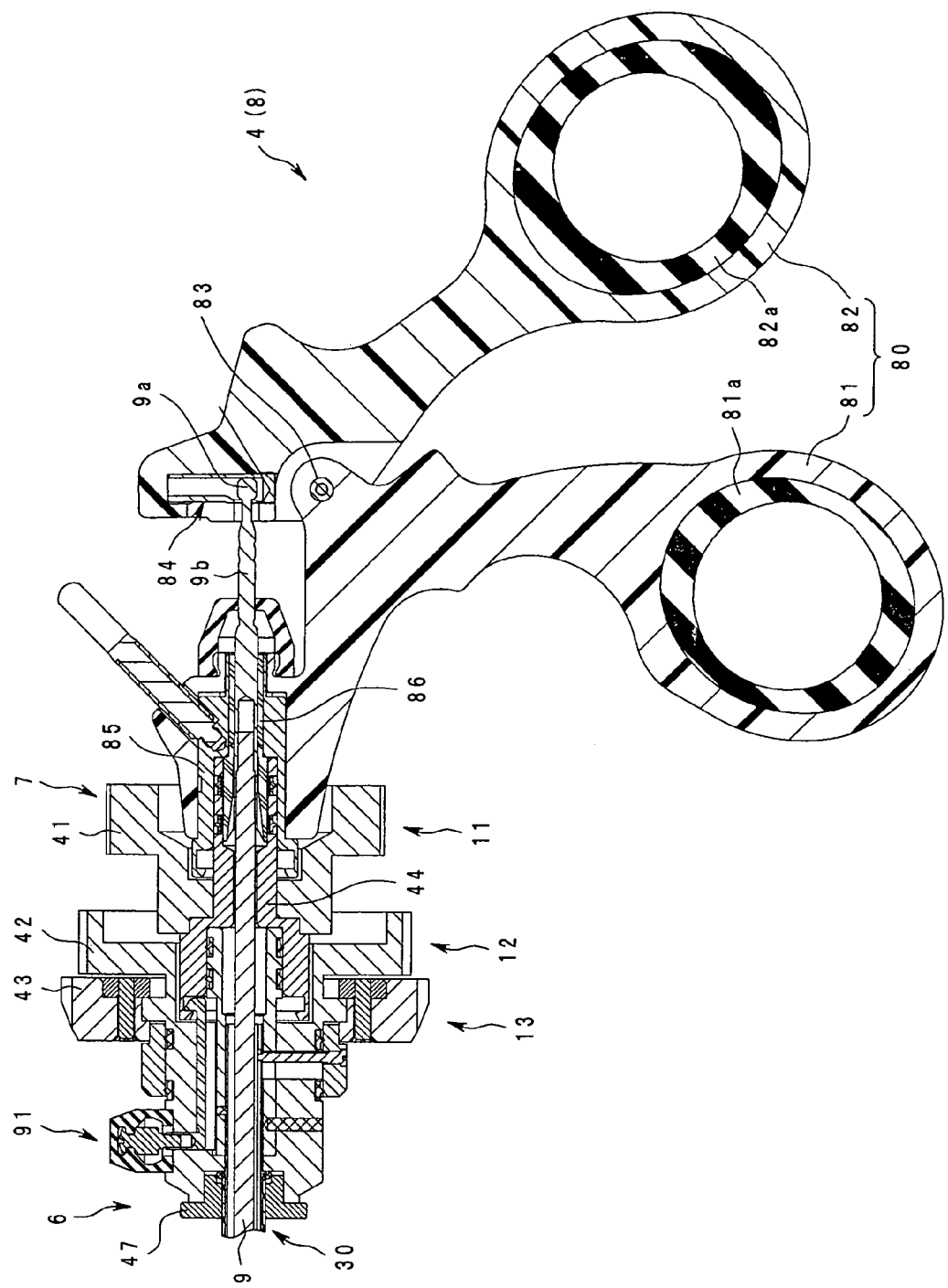
FIG. 20 is a diagram which illustrates the relationship between the pivoting operation of the first knob and the pivoting state of the driving rod bearing.

In concrete terms, as a result of the pivoting operation of the first knob 11, the first knob base 44 that forms an integral part of the first knob main body 41 that forms this first knob 11 pivots as shown in FIG. 20. In this case, the driving rod bearing 86 is caused to pivot in linkage with the pivoting of this first knob base 44. The reason for this is that a construction is used in which the distal end portion of the rotation transmitting guide pin 44b that is disposed on the proximal end portion of the first knob base 44 is inserted and disposed in the guide part 86a of the driving rod bearing 86 that is disposed inside the handle base 85 of the fixed handle 81.

When the driving rod bearing 86 is pivoted, the rotational driving rod 9b is caused to pivot in linkage with the rotation of the driving rod bearing 86 so that the treatment part operating rod 9b also performs a pivoting operation. The reason for this is that the planar parts 9c and 9d of the rotational driving rod 9b are disposed so that these parts contact the contact planes 86c and 86d of the driving rod bearing 86 as described above.

Figure 21:
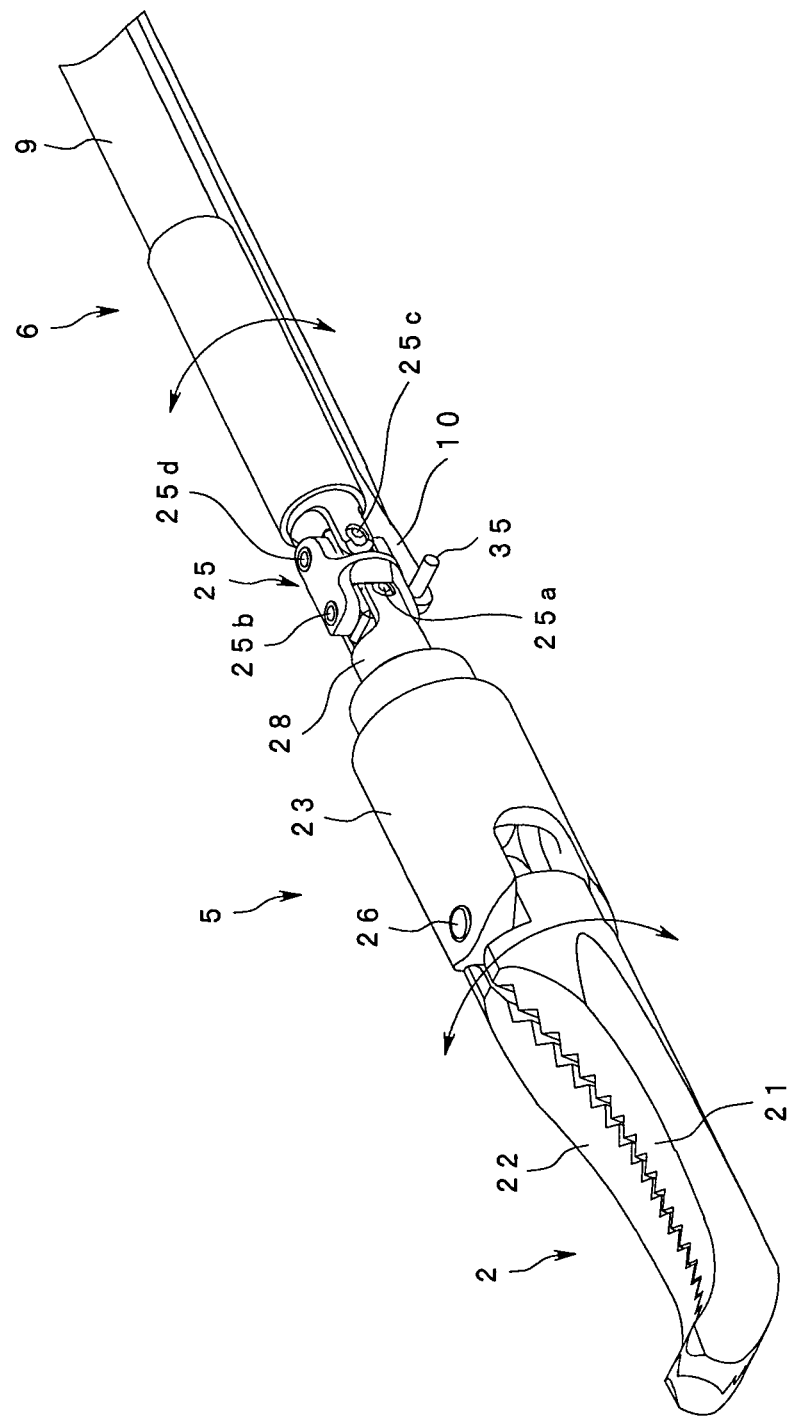
FIG. 21 is a diagram which illustrates the relationship between the pivoting state of the treatment part operating rod and the swiveling state of the treatment part.

In this case, as is shown in FIG. 21, the treatment part 2 which is connected via the joint member 25 and connecting member 28 pivots along with the rotation of the treatment part operating rod 9 indicated by the arrow. Here, the joint member 25 is constructed in the form of universal joints as described above. Accordingly, along with the pivoting motion of the treatment part operating rod 9, this joint member 25 also pivots so that the connecting member 28 begins to pivot.

Furthermore, as a result of the pivoting operation of the connecting member 28, the second treatment piece 22 that is connected to this connecting member 28 via the connecting pin 29 is caused to pivot. Consequently, the first treatment piece 21 which is connected to the second treatment piece via the treatment part pivoting pin 27 pivots. In this case, since this first treatment piece 21 is shaft-supported on the treatment part base 2 via the first treatment piece opening-and-closing pin 26 so that the first treatment piece 21 is free to pivot, the treatment part base 23 is caused to pivot so that the treatment part 2 swivels about the longitudinal axis of the surgical instrument 1.

Accordingly, the treatment part 2 that is connected to the distal end portion of the treatment part operating rod 9 can be caused to swivel about the longitudinal axis of the surgical instrument 1, so that the orientation of this treatment part 2 is set in an arbitrary direction, by turning the first knob 11.

Here, the operation of the treatment part 2 in a case where at least two parts selected from the treatment part opening-and-closing operating part 80, first knob 11, second knob 12 and third knob 13 are manually operated in combination will be described with reference to the attached drawings.

First, the operation that is performed in a case where the pivoting handle 82 is operated in a state in which the treatment part 2 has been pivoted in the range of the angle θ by operating the third knob 13 will be described.

Figure 22:
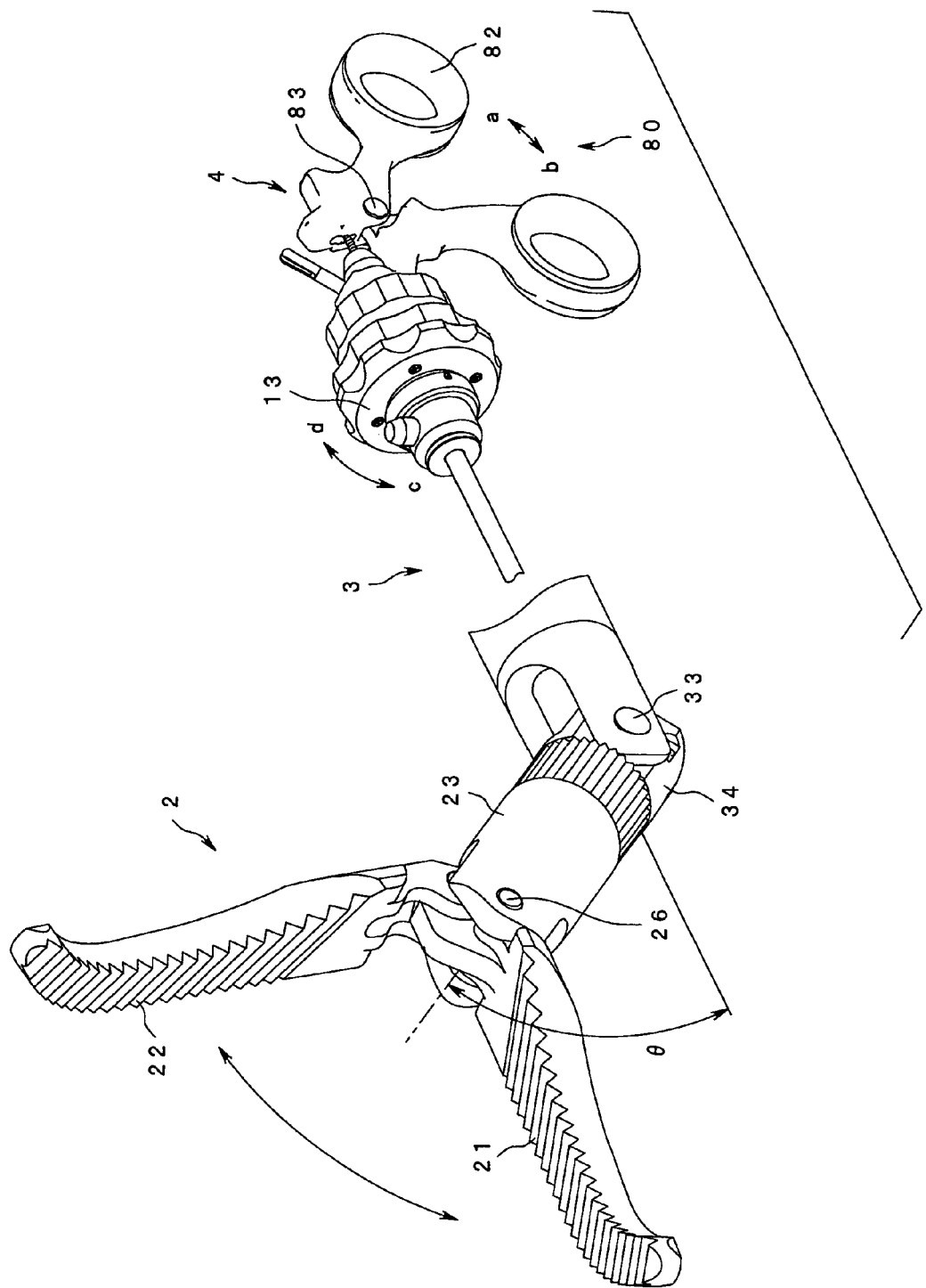
FIG. 22 is a diagram which illustrates the action of the treatment part when the pivoting handle and third knob are operated.

As is shown in FIG. 22, the pivoting handle 82 of the treatment part opening-and-closing operating part 80 is pivoted in a state in which the third knob 13 has been pivoted. Consequently, the treatment part operating rod 9 is caused to advance or retract in a state in which the treatment part 2 is inclined in the range of the angle θ. As a result, the first treatment piece 21 and second treatment piece 22 that constitute the treatment part 2 perform an opening-and-closing action as indicated by the arrows.

Figure 23:
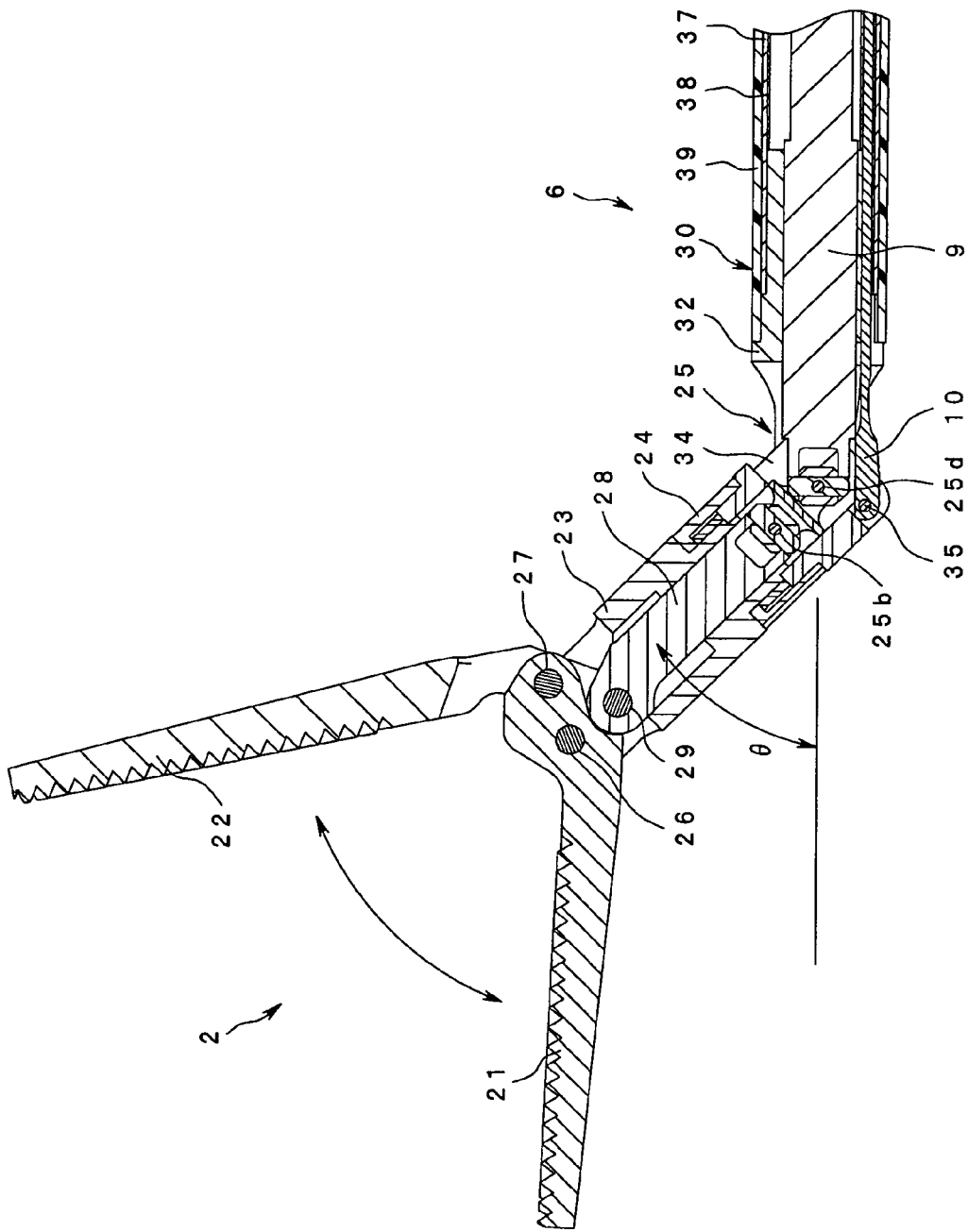
FIG. 23 is a sectional view which illustrates the movement state of the treatment part operating rod and pivoting base operating rod, the pivoting operation of the treatment part, the bent state of the joint member, and the opening-and-closing operation of the first treatment piece and second treatment piece.
Figure 24:
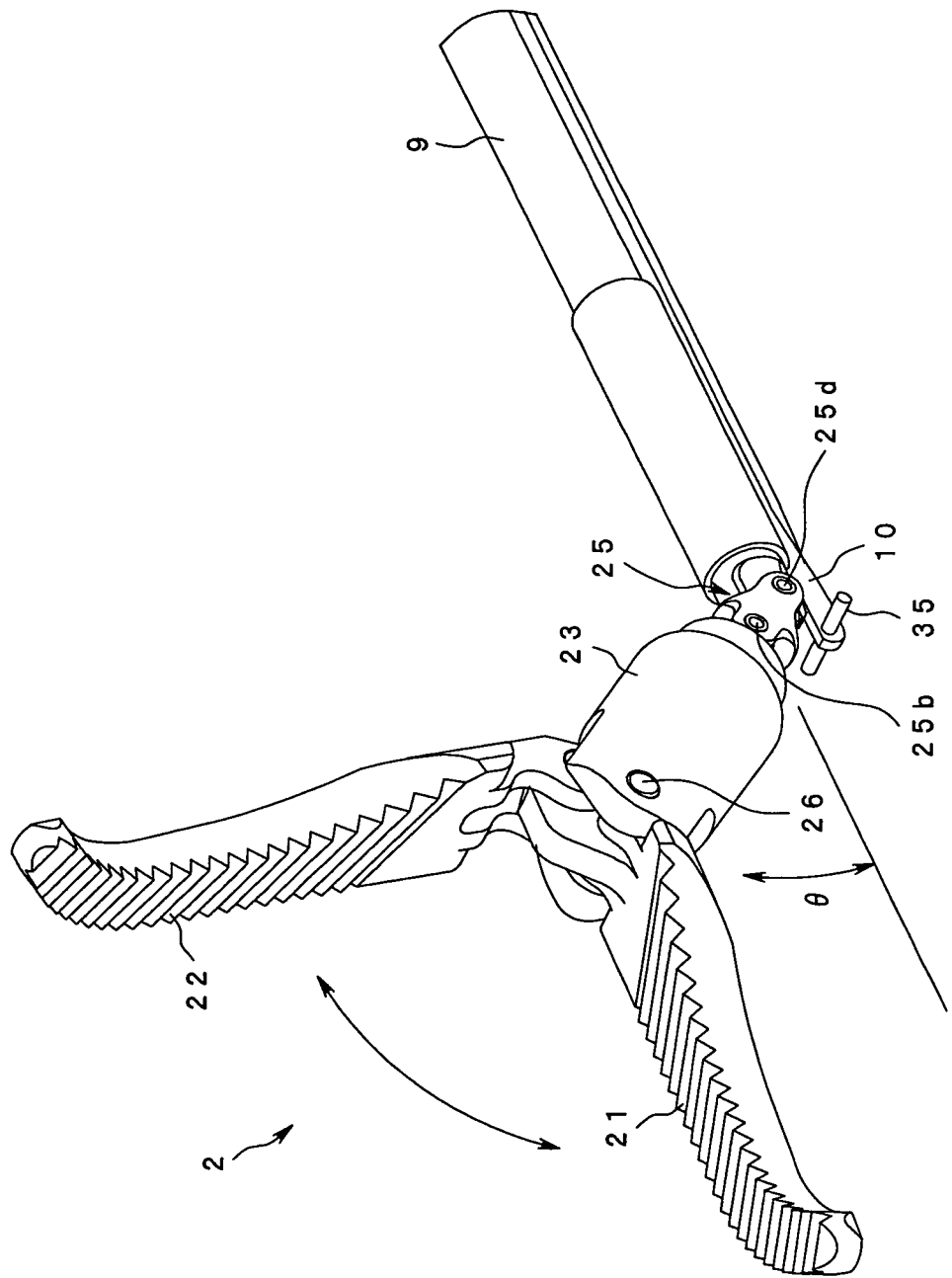
FIG. 24 is a perspective view which illustrates the movement state of the treatment part operating rod and pivoting base operating rod, the pivoting operation of the treatment part, the bent state of the joint member, and the opening-and-closing operation of the first treatment piece and second treatment piece.

In concrete terms, when the treatment part operating rod 9 is caused to advance or retract in a state in which the treatment part has been inclined by (for example) an angle of θ, the joint member 25 and connecting member 28 are also caused to advance or retract is shown in FIGS. 23 and 24. Consequently, the first treatment piece 21 and second treatment piece 22 perform a mutual opening-and-closing action.

In this case, the connecting member 28 and joint member 25 perform a relative pivoting motion about the second joint pin 25b along with the advancing or retracting movement of the treatment part operating rod 9. In addition, this joint member 25 and treatment part operating rod 9 pivot in relative terms about the fourth joint pin 25d, so that the first treatment piece 21 and second treatment piece 22 are caused to perform an opening-and-closing action.

Conversely, furthermore, with the treatment part 2 placed in an open state by the operation of the pivoting handle 82, the third knob 13 is turned. Consequently, the angle θ of the treatment part 2 is varied while the first treatment piece 21 and second treatment piece 22 remain in an open state. Furthermore, the second knob 12 can be turned in a state in which the pivoting handle 82 and the third knob 13 have been operated. Moreover, the pivoting direction of the treatment part 2 can be arbitrarily set by turning this second knob 12.

Next, the operation that is performed in a case where the pivoting handle 82 is operated in a state in which the treatment part 2 has been swiveled by a specified amount by operating the first knob 11 will be described.

Figure 25:
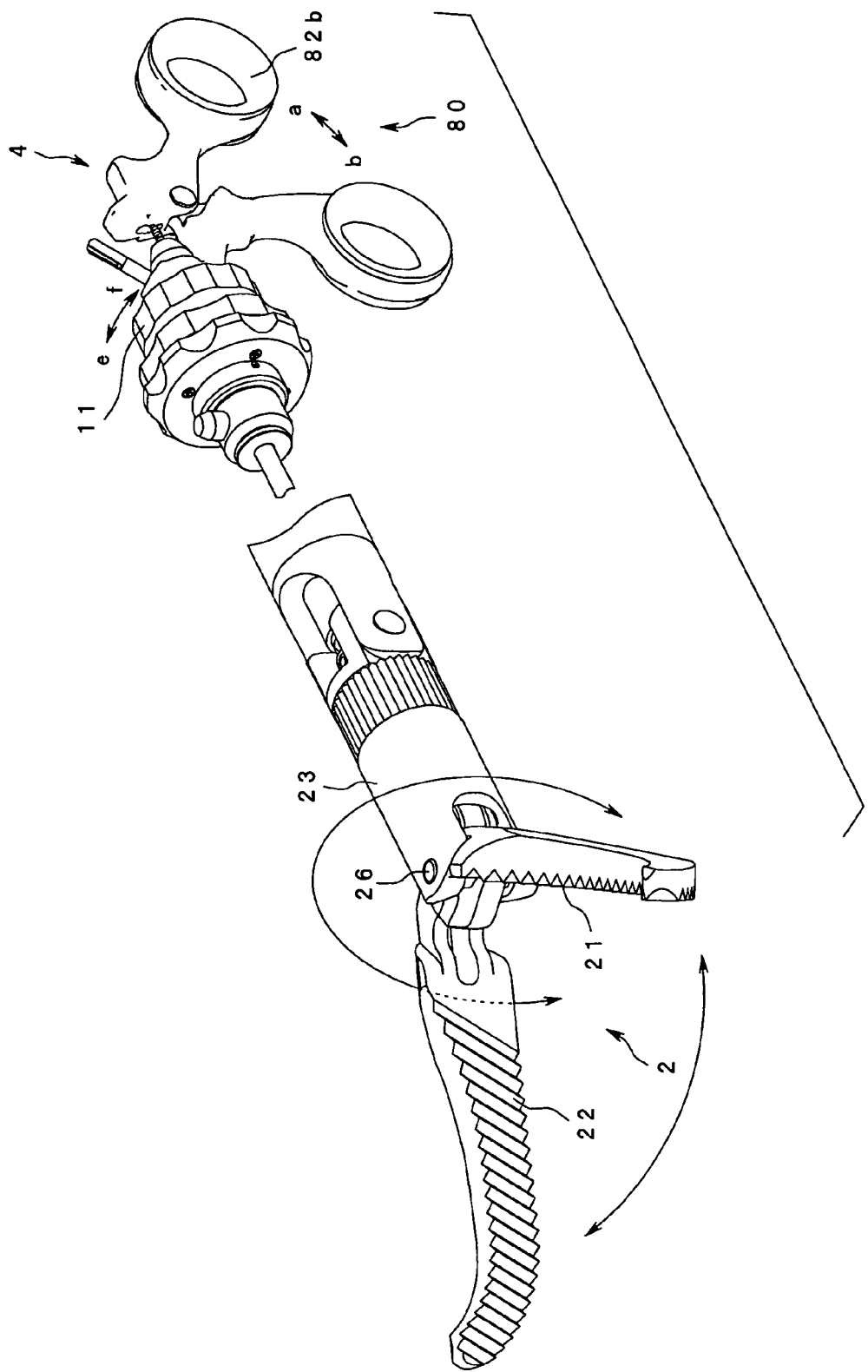
FIG. 25 is a diagram which illustrates the action of the treatment part when the pivoting handle and first knob are operated.

As is shown in FIG. 25, the pivoting handle 82 is operated in a state in which the treatment part 2 has been swiveled by operating the first knob 11. As a result, an opening-and-closing operation of the first treatment piece 21 and second treatment piece 22 that constitute this treatment part 2 can be performed in a state in which the treatment part 2 has been swiveled.

Conversely, with the treatment part 2 placed in an open state by the operation of the pivoting handle 82, the first knob 11 is turned. As a result, the treatment part 2 in an open state can be caused to swivel about the longitudinal axis of the surgical instrument 1, so that the orientation of the treatment part 2 can be set.

Furthermore, the second knob 12 can be turned in a state in which the pivoting handle 82 and the first knob 11 have been operated. The pivoting direction of the treatment part 2 can be set by this turning operation of the second knob 12.

Next, the operation that is performed in a case where the third knob 13 is operated in a state in which the treatment part 2 has been caused to swivel by a specified amount by operating the first knob 11 will be described.

Figure 26:
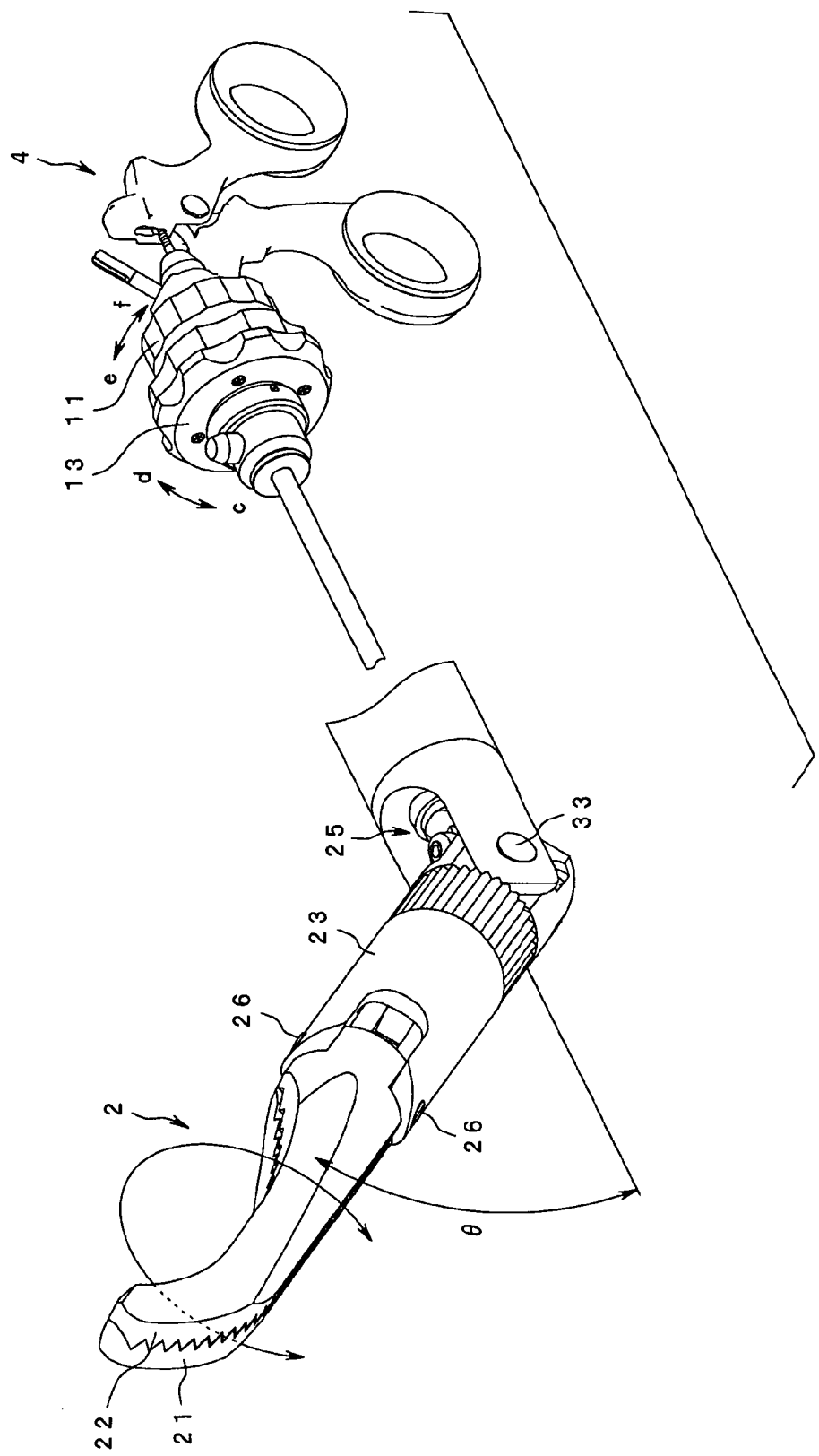
FIG. 26 is a diagram which illustrates the action of the treatment part when the first knob and third knob are operated.

As is shown in FIG. 26, the third knob 13 is operated in a state in which treatment part 2 has been caused to swivel by operating the first knob 11. As a result, the treatment part 2 that was disposed in a horizontal position with respect to the longitudinal axis of the surgical instrument 1 in the swiveled state changes to a state in which this treatment part 2 is inclined by an angle of θ with respect to this longitudinal axis.

Conversely, the first knob 11 is turned in a state in which the treatment part 2 has been inclined by an angle of θ by operating the third knob 13. Consequently, the treatment part 2 in an inclined state performs a swiveling action about its own axis. The reason for this is that the first universal joint 25A disposed on the distal end side of the joint member 25 and the second universal joint 25B disposed on the proximal end side are constructed so that the pivoting motion can be transmitted in a state in which the pivoting axes before and after these universal joints 25A and 25B are inclined by 45 degrees.

Furthermore, the second knob 12 can be turned in a state in which the first knob 11 and third knob 13 have been operated. The pivoting direction of the treatment part 2 can be set by this turning operation of the second knob 12.

Figure 27:
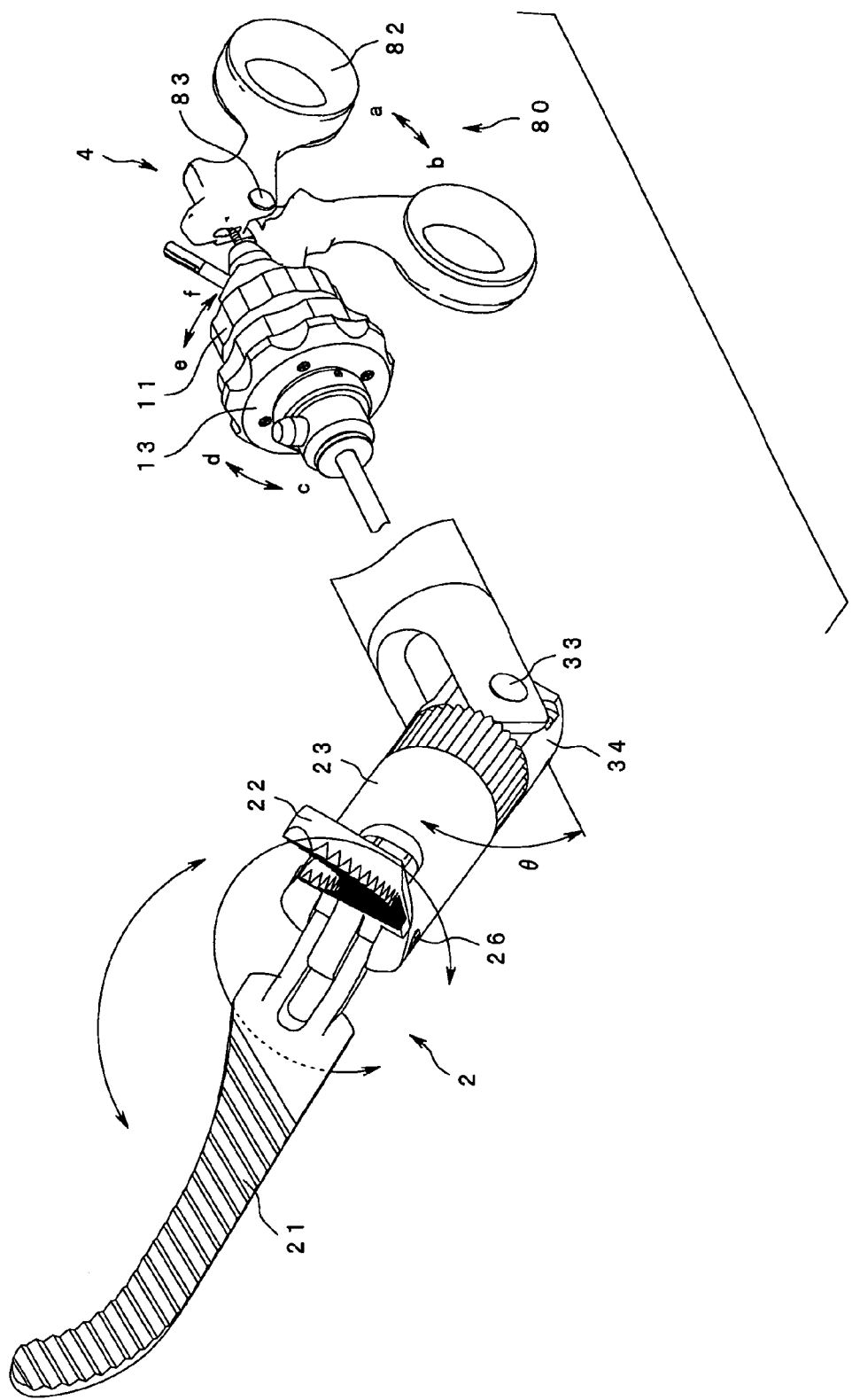
FIG. 27 is a diagram which illustrates the action of the treatment part when the pivoting handle, first knob and third knob are operated.

Furthermore, as is shown in FIG. 27, the pivoting handle 82 is pivoted in a state in which the first knob 11 and third knob 13 have been operated. As a result, the opening and closing operation of the first treatment piece 21 and second treatment piece 22 that constitute the treatment part 2 in a state in which these parts are inclined by an angle of θ with respect to the longitudinal axis can be performed in a swiveled state.

In the present embodiment, the instrument is devised so that the operation in which the treatment part 2 is caused to pivot as described above, the operation in which the treatment part 2 is caused to swivel, the operation in which the pivoting direction of the treatment part 2 is set in a desired orientation and the operation in which the first treatment piece 21 and second treatment piece 22 that constitute the treatment part 2 are caused to open or close can be performed in arbitrary combinations.

As a result, not only the opening and closing operation of the first treatment piece and second treatment piece constituting the treatment part, but also the pivoting of the insertion tube, the pivoting or swiveling of the treatment part and the variation of the positional relationship between the treatment part and the object of gripping to a desired positional relationship, can easily be accomplished by appropriately operating the treatment part opening-and-closing operating part, first knob, second knob and third knob; furthermore, changes in the pivoting attitude of the treatment part or the like caused by unintentional external forces can be reliably prevented.

Furthermore, when the treatment part is operated, this operation can be performed while obtaining a direct sensation of sensory feedback of the force in the fingers of the operator; accordingly, the operability and practicality in actual use can be improved.

Furthermore, the mechanism part that opens and closes the first treatment piece and second treatment piece, the mechanism part that cause the treatment part to pivot, the mechanism part that causes the treatment part to swivel, the mechanism part that causes the insertion tube to pivot and the like can be simplified by constructing these respective mechanism parts with pin connections, screw connections or the like.

Furthermore, since the surgical instrument is constructed so that this instrument can be broken down into a plurality of units, cleaning following use can be accomplished quickly and easily.

Furthermore, if a method of use is employed in which (for example) the third knob 13 is operated with the middle finger while holding the second knob 12 with the index finger when the respective knobs 11, 12 and 13 are operated, an even simpler surgical instrument can be constructed, with no provision of the locking mechanisms for preventing the rotation of the respective knobs.

A second embodiment of the present invention will be described with reference to FIGS. 28 and 29. Furthermore, in this embodiment, constituent parts that are shared with the first embodiment are labeled with the same symbols, and a description of such constituent parts is omitted.

Figure 28:
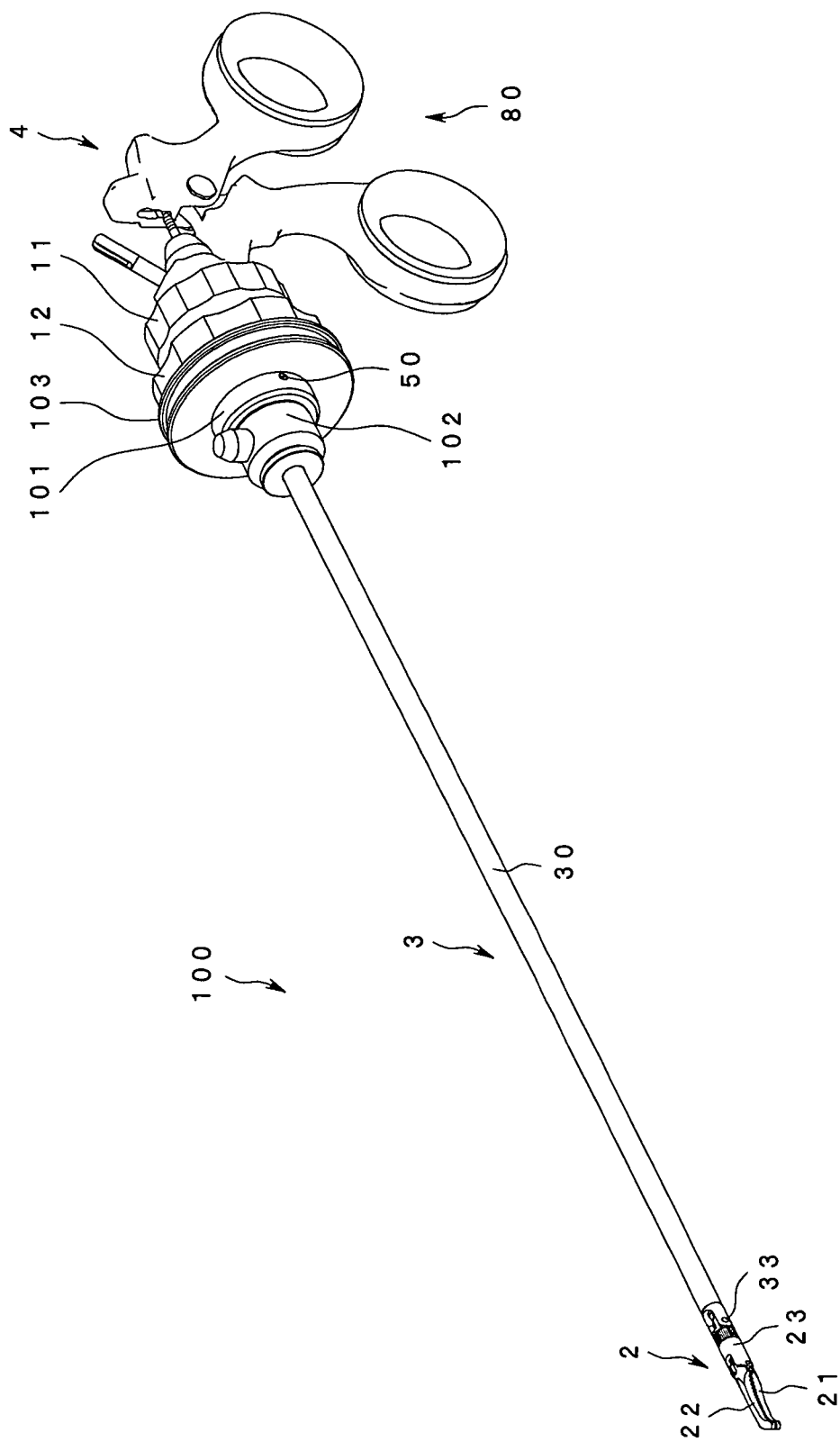
FIG. 28 is a diagram which illustrates a surgical instrument in which the construction of the third knob is different.

As is shown in FIG. 28, the surgical instrument 100 of the present embodiment is constructed with the third knob 103 fastened directly to the advancing and retracting member 101. This advancing and retracting member 101 is disposed on the second knob main body 102 so that this member is free to advance and retract. Furthermore, the advancing and retracting member 101 and the pivoting base operating rod (not shown in the drawings) are integrally connected and fastened by a connecting and fastening screw 50.

Accordingly, in the first embodiment, a construction was used in which the pivoting base operating rod 10 was caused to advance and retract by turning the third knob 13. In the present embodiment, on the other hand, the instrument is devised so that the advancing and retracting member 101 is caused to advance or retract with respect to the second knob main body 102, thus causing the pivoting base operating rod 10 to advance or retract, by causing the third knob 103 to advance or retract in the direction indicated by the arrow g or the direction indicated by the arrow h as shown in FIG. 29.

Figure 29:
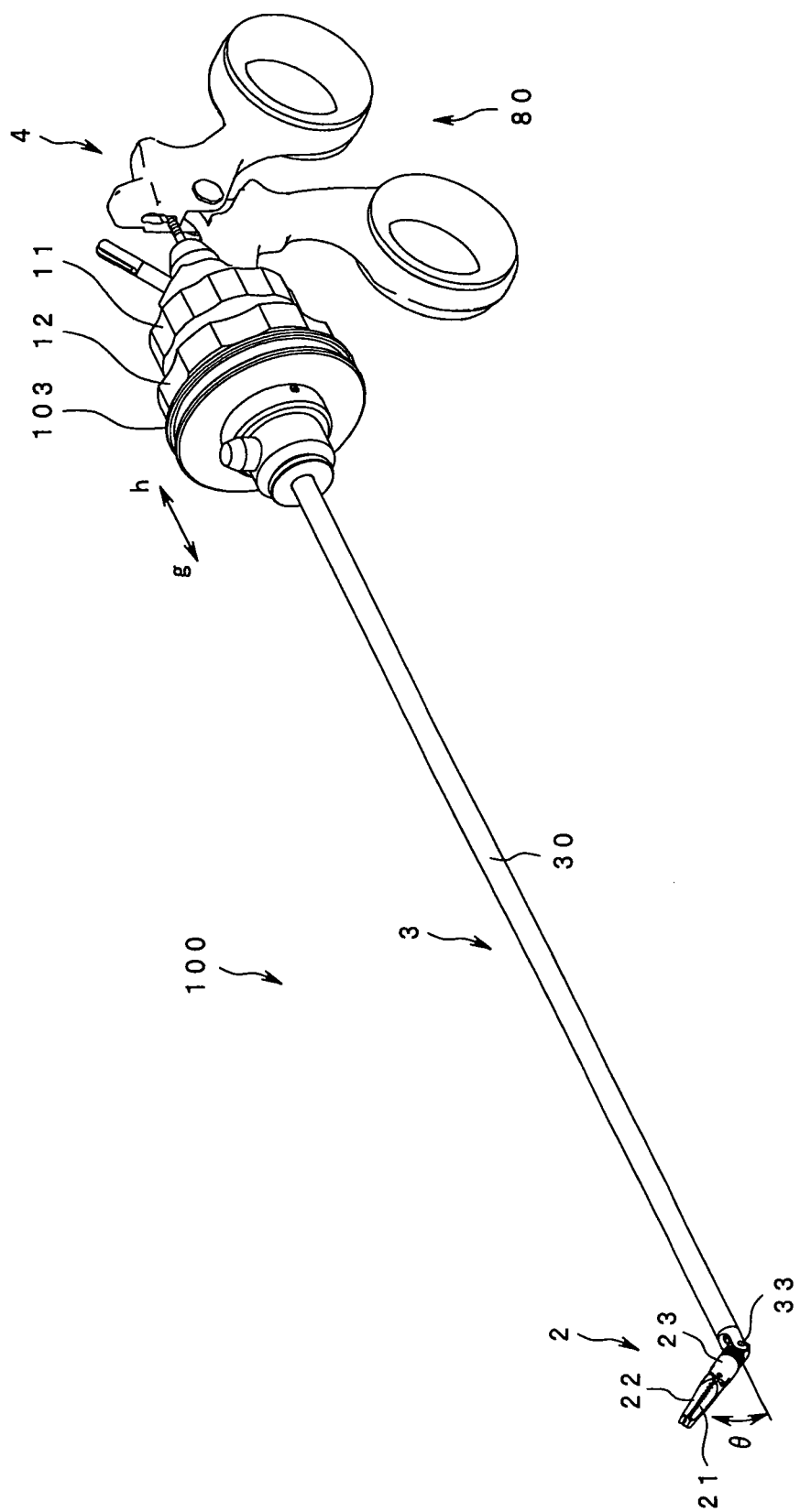
FIG. 29 is a diagram which illustrates the operation of the surgical instrument.

In other words, as is shown in FIG. 29, the advancing and retracting member 101 which forms an integral part of the third knob 103 is caused by advance or retract by causing the third knob 103 to advance or retract, so that the pivoting base 34 performs a pivoting operating through the range of the angle θ as indicated by the arrows in the drawings.

Thus, the pivoting operation of the treatment part can be performed more quickly by integrally fastening the third knob to an advancing and retracting member which is disposed on the second knob main body so that this advancing and retracting member is free to advance and retract.

Furthermore, the present invention is not limited to only the embodiments described above; various modifications are possible within limits that involve no departure from the spirit of the present invention.

Having described the preferred embodiments of the invention referring to the accompanying drawings, it should be understood that the present invention is not limited to those precise embodiments, and that various changes and modifications thereof could be made by one skilled in the art without departing from the spirit or scope of the invention as defined in the appended claims.

What is claimed is:

1. A surgical instrument comprising:
    a treatment part opening-and-closing operating part comprising a fixed handle and a pivoting handle, which also serves as a gripping part;
    an elongated treatment part operating rod having rigidity, which is connected to the pivoting handle of the treatment part opening-and-closing operating part, which is arranged to be rotatable about an axis of the elongated treatment part operating rod, and which advances and retracts in accordance with the operation of the pivoting handle;
    an insertion part through which the elongated treatment part operating rod is inserted;
    a pivoting base which is pivotably shaft-supported on a distal end portion of the insertion part via a pivoting shaft disposed in a direction perpendicular to a longitudinal axis of the insertion part;
    an elongated pivoting base operating rod having rigidity, a distal end portion of which is connected to the pivoting base, and which causes the pivoting base to pivot about the pivoting shaft by an advancing and retracting motion;

a treatment part base which is held to allow rotation about an axis of the pivoting base with respect to the pivoting base, and on which a surgical treatment part which performs an opening-and-closing action in accordance with the advancing and retracting operation of the elongated treatment part operating rod is disposed; and a joint member having two sets of universal joints and constituting a connecting part having rigidity that connects the elongated treatment part operating rod and a connecting member which is pivotably shaft-supported at one end of the surgical treatment part disposed on the treatment part base by a connecting pin in a parallel positional relationship with the pivoting shaft, each of the two sets of universal joints comprising a pair of ordinary hinges oriented at 90° relative to each other, the joint member transmitting pivoting motion of the elongated treatment part operating rod about the axis of the elongated treatment part operating rod to the connecting member.

2. The surgical instrument according to claim 1, wherein the surgical treatment part has a construction comprising a first treatment piece and a second treatment piece, and the first treatment piece and second treatment piece are varied between a closed state constituting a first terminating state and a second terminating state constituting a maximum open state by causing the treatment part operating rod to advance or retract by operating the pivoting handle.

3. The surgical instrument according to claim 2, wherein the joint member has a construction in which a center of the universal joint positioned on the distal end side of the joint member coincides with an axial center of the pivoting shaft when the surgical treatment part is in a first terminating state, and the center of the universal joint positioned on the proximal end side of the joint member coincides with the axial center of the pivoting shaft when the surgical treatment part is in a second terminating state.

4. The surgical instrument according to claim 1, wherein the treatment part operating rod is detachably connected to the pivoting handle of the treatment part opening-and-closing operating part.

5. The surgical instrument according to claim 1, wherein the treatment part base is detachably connected to the pivoting base.

6. The surgical instrument according to claim 1, wherein
a first operating knob which swivels the surgical treatment part by causing the elongated treatment part operating rod to pivot,
a second operating knob which varies the pivoting direction of the free-pivoting pivoting base by causing the insertion part to pivot, and
a third operating knob which causes the pivoting base to pivot about the pivoting shaft by causing the elongated pivoting base operating rod to advance or retract are disposed on a proximal end portion of the insertion part.

7. The surgical instrument according to claim 6, wherein, diameter dimensions of the first operating knob, the second operating know, and the third operating knob are formed so that these diameter dimensions expand toward the distal end portion of the insertion part from a side of the treatment part opening-and-closing operating part.

* * * * *